US010004811B2

(12) United States Patent
Crystal et al.

(10) Patent No.: US 10,004,811 B2
(45) Date of Patent: Jun. 26, 2018

(54) DEVELOPMENT OF A HIGHLY EFFICIENT SECOND GENERATION NICOTINE-CONJUGATE VACCINE TO TREAT NICOTINE ADDICTION

(71) Applicant: Cornell University, Ithaca, NY (US)

(72) Inventors: Ronald G. Crystal, New York, NY (US); Jonathan B. Rosenberg, Cranbury, NJ (US); Bishnu P. De, New Hyde Park, NY (US); Martin J. Hicks, New York, NY (US); Stephen M. Kaminsky, Bronx, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days. days.

(21) Appl. No.: 14/511,790

(22) PCT Filed: Mar. 14, 2013

(86) PCT No.: PCT/US2013/031409
§ 371 (c)(1),
(2) Date: Oct. 10, 2014

(87) PCT Pub. No.: WO2013/154744
PCT Pub. Date: Oct. 17, 2013

(65) Prior Publication Data
US 2015/0297739 A1 Oct. 22, 2015

Related U.S. Application Data

(60) Provisional application No. 61/623,908, filed on Apr. 13, 2012.

(51) Int. Cl.
*A61K 47/64* (2017.01)
*A61K 47/48* (2006.01)

(52) U.S. Cl.
CPC ........ *A61K 47/4833* (2013.01); *A61K 47/646* (2017.08)

(58) Field of Classification Search
None
See application file for complete search history.

(56) References Cited

U.S. PATENT DOCUMENTS

| 4,123,431 | A | 10/1978 | Soffer et al. |
| 4,197,237 | A | 4/1980 | Leute et al. |
| 4,863,457 | A | 9/1989 | Lee |
| 5,378,475 | A | 1/1995 | Smith et al. |
| 5,443,505 | A | 8/1995 | Wong et al. |
| 5,801,030 | A | 9/1998 | McVey et al. |
| 5,837,511 | A | 11/1998 | Falck-Pedersen et al. |
| 5,849,561 | A | 12/1998 | Falck-Pedersen et al. |
| 5,876,727 | A | 3/1999 | Swain et al. |
| 6,232,082 | B1 * | 5/2001 | Ennifar .............. A61K 39/0013 424/175.1 |
| 6,932,971 | B2 * | 8/2005 | Bachmann ......... A61K 39/0013 424/184.1 |
| 7,094,398 | B1 | 8/2006 | Lieber et al. |
| 2003/0091593 | A1 | 5/2003 | Bachmann et al. |
| 2003/0138772 | A1 * | 7/2003 | Gao ..................... C07K 14/005 435/5 |
| 2004/0059094 | A1 | 3/2004 | Bachmann et al. |
| 2006/0034805 | A1 * | 2/2006 | Fang ..................... C07K 16/00 424/93.2 |
| 2007/0243195 | A1 | 10/2007 | Minke et al. |
| 2008/0026000 | A1 | 1/2008 | Ennifar et al. |
| 2011/0086063 | A1 | 4/2011 | Crystal et al. |
| 2011/0123541 | A1 * | 5/2011 | Bachmann ............. C07K 16/00 424/142.1 |
| 2011/0305720 | A1 | 12/2011 | Patel et al. |
| 2012/0232133 | A1 * | 9/2012 | Balazs ............... C07K 16/1045 514/44 R |

FOREIGN PATENT DOCUMENTS

| WO | WO 1997/012986 A2 | 4/1997 | |
| WO | WO 1997/021451 A1 | 6/1997 | |
| WO | WO 9720051 A2 * | 6/1997 | .......... C07K 14/005 |
| WO | WO 1998/053087 A1 | 11/1998 | |
| WO | WO 1999/061054 A1 | 12/1999 | |
| WO | WO 02058635 A2 * | 8/2002 | .......... C07D 207/06 |
| WO | WO 03048185 A2 * | 6/2003 | .......... C07K 14/515 |
| WO | WO 2004/009116 A2 | 1/2004 | |
| WO | WO 2007055928 A1 * | 5/2007 | .......... C07D 261/08 |
| WO | WO 2008/140474 A1 | 11/2008 | |
| WO | WO 2009/117656 A2 | 9/2009 | |
| WO | WO 2009/149252 A1 | 12/2009 | |
| WO | WO 2011/116189 A1 | 9/2011 | |

(Continued)

OTHER PUBLICATIONS

Carrera MF, Ashley JA, Hoffman TZ, Isomura S, Wirsching P, Koob GF, Janda KD. Investigations using immunization to attenuate the psychoactive effects of nicotine. Bioorg Med Chem. Feb. 1, 2004;12(3):563-70.*
Isomura S, Wirsching P, Janda KD. An immunotherapeutic program for the treatment of nicotine addiction: hapten design and synthesis. J Org Chem. Jun. 15, 2001;66(12):4115-21.*
Abad et al., Comparison of a Monoclonal Antibody-Based Enzyme-Linked Immunosorbent Assay and Gas Chromatography for the Determination of Nicotine in Cigarette Smoke Condensates, *Analytical Chemistry*, 65(22): 3227-3231 (1993).
Alberg et al., Epidemiology of Lung Cancer: Looking to the Future, *Journal of Clinical Oncology*, 23(14): 3175-3185 (2005).
Ausubel et al., *Short Protocols in Molecular Biology*, 5th Ed., John Wiley & Sons, New York (2002) (Table of Contents only).
Benowitz et al., Daily intake of nicotine during cigarette smoking, *Clin. Pharmacol. Ther.*, 35(4): 499-504 (1984).

(Continued)

*Primary Examiner* — Stacy B Chen
(74) *Attorney, Agent, or Firm* — Leydig, Voit & Mayer, Ltd.

(57) ABSTRACT

The invention is directed to a conjugate which comprises an isolated adenovirus hexon protein coupled to nicotine or a nicotine analog, as well as a method of inducing an immune response against nicotine in a human by using the conjugate.

13 Claims, 7 Drawing Sheets

(56) References Cited

FOREIGN PATENT DOCUMENTS

Figure 1A:
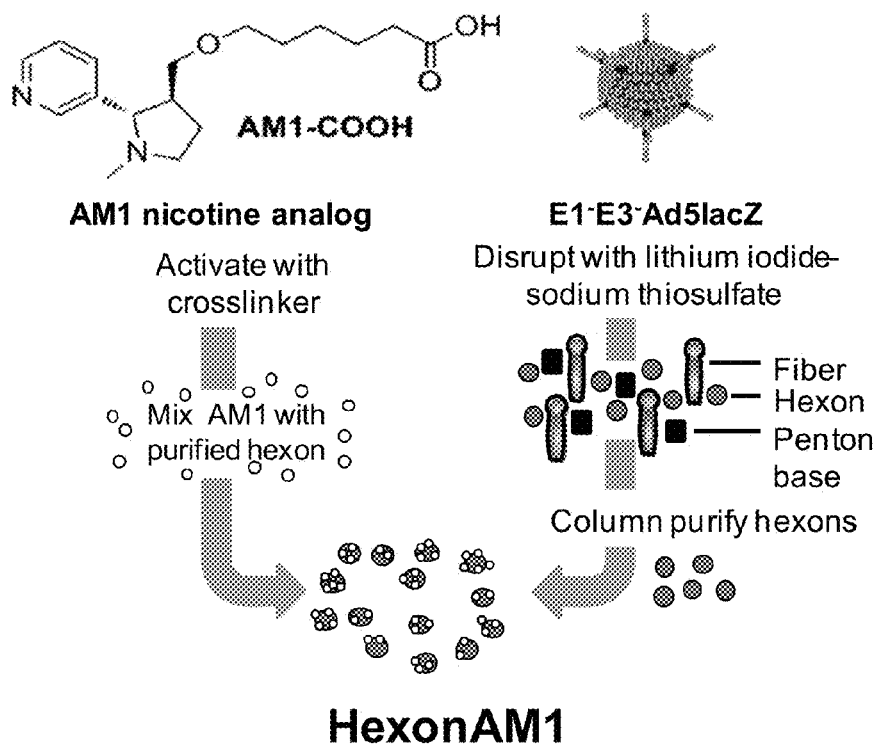

| WO | WO 2011116189 A1 * | 9/2011 | ......... A61K 39/0013 |
| WO | WO 2011127989 A1 * | 10/2011 | ......... A61K 39/0013 |

OTHER PUBLICATIONS

Benowitz, Pharmacology of Nicotine: Addiction, Smoking-Induced Disease, and Therapeutics, *Annu. Rev. Pharmacol. Toxicol.*, 49: 57-71 (2009).
Blanco-Cedres et al., Relation of Cigarette Smoking to 25-Year Mortality in Middle-aged Men with Low Baseline Serum Cholesterol, *American Journal of Epidemiology*, 155(4): 354-360 (2002).
Boulanger et al., Characterization of Adenovirus Protein IX, *J. Gen. Virol.*, 44: 783-800 (1979).
Boulanger, et al., Comparative Optical Properties of Free and Assembled Hexon Capsomeres of Human Adenovirus Type 2, *FEBS Letters*, 85(1): 52-56 (1978).
Carrera et al., Suppression of psychoactive effects of cocaine by active immunization, *Nature*, 378: 727-730 (1995).
Castro et al., Nicotine Antibody Production: Comparison of Two Nicotine Conjugates in Different Animal Species, *Biochemical and Biophysical Research Communications*, 67(2): 583-589 (1975).
Castro et al., Nicotine Antibodies : Comparison of Ligand Specificities of Antibodies Produced against Two Nicotine Conjugates, *Eur. J. Biochem.*, 104: 331-340 (1980).
Center for Disease Control and Prevention, Morbidity and Mortality Weekly Report, *Centers for Disease Control*, 61(44):889-894 (2012).
Cerny et al., Preclinical Development of a Vaccine Against Smoking, *Onkologie*, 25: 406-411 (2002).
Church et al., Free-Radical Chemistry of Cigarette Smoke and Its Toxicological Implications, *Environmental Health Perspectives*, 64: 111-126 (1985).
Crawford-Miksza et al., Analysis of 15 Adenovirus Hexon Proteins Reveals the Location and Structure of Seven Hypervariable Regions Containing Serotype-Specific Residues, *Journal of Virology*, 70(3): 1836-1844 (1996).
De Villiers et al., Active Immunization against Nicotine Suppresses Nicotine-Induced Dopamine Release in the Rat Nucleus accumbens Shell, *Respiration*, 69: 247-253 (2002).
Dick et al., Glycoconjugates of Bacterial Carbohydrate Antigens, Conjugate Vaccines, *Contrib. Microbiol. Immunol.*, 10: 48-114 (1989).
Fiore et al., Treating Tobacco Use and Dependence: 2008 Update, U.S. Dept. of Health and Human Services, Public Health Service, May 2008.
Haase et al., The Immunogenicity of Adenovirus Type 5 Structural Proteins, *The Journal of Immunology*, 108(2): 483-485 (1972).
Harlow and Lane, *Antibodies: A Laboratory Manual*, Cold Spring Harbor Laboratory, Cold Spring Harbor, N.Y. (1988) (Table of Contents only).
Hatsukami et al., Immunogenicity and Smoking Cessation Outcomes for a Novel Nicotine Immunotherapeutic, *Clin. Pharmacol. Ther.*, 89(3): 392-399 (2011).
Hermanson, Bioconjugate Techniques, Academic Press (1996).
Hicks et al., Cocaine Analog Coupled to Disrupted Adenovirus: A Vaccine Strategy to Evoke High-titer Immunity Against Addictive Drugs, *Molecular Therapy*, 19(3), 612-619 (2011).
Hicks et al., AAV-Directed Persistent Expression of a Gene Encoding Anti-Nicotine Antibody for Smoking Cessation, *Science Translational Medicine*, 4: 140ra87 (2012).
Hieda et al., Vaccination against nicotine during continued nicotine administration in rats: immunogenicity of the vaccine and effects on nicotine distribution to brain, *International Journal of Immunopharmacology*, 22: 809-819 (2000).
Hoffmann et al., Smoking and Tobacco Control Monograph No. 9, Chemistry and Toxicology (NCI), 9: 55-104 (2011).
Hylkema et al., Tobacco use in relation to COPD and Asthma, *European Respiratory Journal*, 29(3): 438-445 (2007).

Isomura et al., An Immunotherapeutic Program for the Treatment of Nicotine Addiction: Hapten Design and Synthesis, *J. Org. Chem.*, 66: 4115-4121 (2001).
Kasel et al., Antigenicity of Alum and Aqueous Adenovirus Hexon Antigen Vaccines in Man, *The Journal of Immunology*, 107(3): 916-919 (1971).
Kramp et al., Liposomal Enhancement of the Immunogenicity of Adenovirus Type 5 Hexon and Fiber Vaccines, *Infection and Immunity*, 25(2): 771-773(1979).
Langone et al., Nicotine and Its Metabolites. Radioimmunoassays for Nicotine and Cotinine, *Biochemistry*, 12(24): 5025-5030 (1973).
Langone et al.,Radioimmunoassay of Nicotine, Cotinine, and γ-(3-Pyridy)-oxo-N-methylbutyramide, *Methods in Enzymology*, 84: 628-640 (1982).
Le Houezec, Role of nicotine pharmacokinetics in nicotine addiction and nicotine replacement therapy: a review, *The International Journal of Tuberculosis and Lung Disease*, 7(9): 811-819 (2003).
Lesage et al., Current Status of Immunologic Approaches to Treating Tobacco Dependence: Vaccines and Nicotine-specific Antibodies, *The AAPS Journal*, 8(1): E65-E75 (2006).
Lichty et al., Comparison of affinity tags for protein purification, *Protein Expression and Purification*, 41: 98-105 (2005).
Liepold et al., Viral Capsids as MRI Contrast Agents, *Magnetic Resonance in Medicine*, 58: 871-879 (2007).
Leopold et al., Fluorescent Virions: Dynamic Tracking of the Pathway of Adenoviral Gene Transfer Vectors in Living Cells, *Human Gene Therapy*, 9: 367-378 (1998).
Lindblom et al., Active Immunization against Nicotine Prevents Reinstatement of Nicotine-Seeking Behavior in Rats, *Respiration*, 69: 254-260 (2002).
Maskos et al., Nicotine reinforcement and cognition restored by targeted expression of nicotinic receptors, *Nature*, 436: 103-107 (2005).
Matthews et al., Optimization of capsid-incorporated antigens for a novel adenovirus vaccine approach, *Virology Journal*, 5: 98 (2008).
Matthews et al., HIV Antigen Incorporation within Adenovirus Hexon Hypervariable 2 for a Novel HIV Vaccine Approach, *PLoS One*, 5(7): e11815 (2010).
Matsushita et al., Conjugate of Bovine Serum Albumin With Nicotine, *Biochemical Biophysical Research Communications*, 57(4): 1006-1010 (1974).
Maurer et al., A therapeutic vaccine for nicotine dependence: preclinical efficacy, and phase I safety and immunogenicity, *European Journal of Immunology*, 35: 2031-2040 (2005).
Maurer et al., Vaccination against nicotine: an emerging therapy for tobacco dependence, *Expert Opinion on Investigational Drugs*, 16(11): 1775-1783 (2007).
McConnell et al., Characterization of a Permissive Epitope Insertion Site in Adenovirus Hexon, *Journal of Virology*, 80(11): 5361-5370 (2006).
Meijler et al., A New Strategy for Improved Nicotine Vaccines Using Conformationally Constrained Haptens, *Journal of American Chemical Society*, 125: 7164-7165 (2003).
Migneault et al., Glutaraldehyde: behavior in aqueous solution, reaction with proteins, and application to enzyme crosslinking, *BioTechniques*, 37(5): 790-802 (2004).
Miyazawa et al., Fiber Swap between Adenovirus Subgroups B and C Alters Intracellular Trafficking of Adenovirus Gene Transfer Vectors, *Journal of Virology*,73(7): 6056-6065 (1999).
Molinier-Frenkel et al., Adenovirus Hexon Protein Is a Potent Adjuvant for Activation of a Cellular Immune Response, *Journal of Virology*, 76(1): 127-135 (2002).
Moreno et al., Immunopharmacotherapy: Vaccination strategies as a treatment for drug abuse and dependence, *Pharmacology, Biochemistry and Behavior*, 92: 199-205 (2009).
Moreno et al., A Critical Evaluation of a Nicotine Vaccine within a Self-Administration Behavioral Model, *Molecular Pharmaceutics*, 7(2): 431-441 (2010).
Nermut, *The Architecture of Adenoviruses*, pp. 5-34, in H. S. Ginsberg (ed.), "The Adenoviruses," Plenum Press, New York, N.Y. (1984).

(56) References Cited

OTHER PUBLICATIONS

Neurath et al., Disruption of Adenovirus Type 7 by Lithium Iodide Resulting in the Release of Viral Deoxyribonucleic Acid, *Journal of Virology*, 5(2), 173-178 (1970).
Noguchi et al., Conjugate of Nicotine and Cotinine to Bovine Serum Albumin, *Biochemical and Biophysical Research Communications*, 83(1): 83-86 (1978).
Ogihara et al., Design of three-dimensional domain-swapped dimmers and fibrous oligomers, *Proc. Natl. Acad. Sci. USA*, 98(4): 1404-1409 (2001).
Palma et al., Adenovirus particles that display the Plasmodium falciparum circumsporozoite protein NANP repeat induce sporozoite-neutralizing antibodies in mice, *Vaccine*, 29: 1683-1689 (2011).
Pentel et al., A Nicotine Conjugate Vaccine Reduces Nicotine Distribution to Brain and Attenuates Its Behavioral and Cardiovascular Effects in Rats, *Pharmacology, Biochemistry and Behavior*, 65(1): 191-198 (2000).
Pollack, A., Antismoking Vaccine Fails in Late Trial, The New York Times (Jul. 18, 2011).
Polosa et al., Treatment of nicotine addiction: present therapeutic options and pipeline developments, Trends in Pharmacological Sciences, 32(5): 281-289 (2011).
Pryor et al., Oxidants in Cigarette Smoke—Radicals, Hydrogen Peroxide, Peroxynitrate, and Peroxynitrite, *Annals of the New York Academy of Sciences*, 686: 12-27 (1993).
Remington: The Science and Practice of Pharmacy, 21st Edition, Lippincott Williams & Wilkins, Philadelphia, PA (2001).
Rose et al., Arterial nicotine kinetics during cigarette smoking and intravenous nicotine administration: implications for addiction, *Drug and Alcohol Dependence*, 56: 99-107 (1999).
Rosenfeld et al., In Vivo Transfer of the Human Cystic Fibrosis Transmembrane Conductance Regulator Gene to the Airway Epithelium, *Cell*, 68: 143-155 (1992).
Sambrook et al., *Molecular Cloning, a Laboratory Manual, Fourth Edition*, Cold Spring Harbor Laboratory Press, Cold Spring Harbor, N.Y. (2001) (Table of Contents only).
Sebelius, K., How Tobacco Smoke Causes Disease:the Biology and Behavioral Basis for Smoking-Attributable Disease: a Report of the Surgeon General, *U.S. Dept. of Health and Human Services* (2010).
Singh et al., Designer adenoviruses for nanomedicine and nanodiagnostics, *Trends in Biotechnology*, 27(4): 220-229 (2009).
Tammimaki et al., Recent advances in gene manipulation and nicotinic acetylcholine receptor biology, *Biochemical Pharmacology*, 82(8): 808-19 (2011).
Tuncok et al., Inhibition of Nicotine-Induced Seizures in Rats by Combining Vaccination Against Nicotine With Chronic Nicotine Infusion, *Experimental and Clinical Psychopharmacology*, 9(2): 228-234 (2001).
Vasalatiy et al., Labeling of Adenovirus Particles with PARACEST Agents, *Bioconjugate Chem.*, 19(3): 598-606 (2008).
Wong, Chemistry of Protein Conjugation and Cross-Linking (CRC Press, Inc., 1991).
Worgall et al., Protection against *P. aeruginosa* with an adenovirus vector containing an OprF epitope in the capsid, *The Journal of Clinical Investigation*, 115(5): 1281-1289 (2005).
Yoshioka et al., Tat conjugation of adenovirus vector broadens tropism and enhances transduction efficiency, *Life Sciences*, 83: 747-755 (2008).
Amidi et al., "N-Trimethyl chitosan (TMC) Nanoparticles Loaded with Influenza Subunit Antigen for Intranasal Vaccination: Biological Properties and Immunogenicity in a Mouse Model," *Vaccine*, 25: 144-153 (2007).
Anton et al., "A Novel Bivalent Morphine/Heroin Vaccine that Prevents Relapse to Heroin Addiction in Rodents," *Vaccine*, 24: 3232-3240 (2006).
Barouch et al., "Adenovirus Vector-Based Vaccines for Human Immunodeficiency Virus Type 1," *Human Gene Therapy*, 16: 149-156 (2005).
Basak et al., "Modifying Adenoviral Vectors for Use as Gene-Based Cancer Vaccines," *Viral Immunology*, 17(2): 182-196 (2004).
Bayer et al., "Vaccination with an Adenoviral Vector That Encodes and Displays a Retroviral Antigen Induces Improved Neutralizing Antibody and CD4+ T-Cell Responses and Confers Enhanced Protection", *Journal of Virology*, 84(4): 1967-1976 (2009).
Beerli et al., "Isolation of Human Monoclonal Antibodies by Mammalian Cell Display," *Proc. Natl. Acad. Sci. U.S.A.*, 105(38): 14336-14341 (2008).
Benuck et al., "Pharmacokinetics of Systemically Administered Cocaine and Locomotor Stimulation in Mice," *The Journal of Pharmacology and Experimental Therapeutics*, 243(1): 144-149 (1987).
Bhavsar et al., "Polymeric Nano- and Microparticle technologies for Oral Gene Delivery," *Expert Opin. Drug Deliv.*, 4(3): 197-213 (2007).
Bielinska et al., "Mucosal Immunization with a Novel Nanoemulsion-Based Recombinant Anthrax Protective Antigen Vaccine Protects Against *Bacillus anthracis* Spore Challenge," *Infection and Immunity*, 75(8): 4020-4029 (2007).
Bonese, et al., "Changes in Heroin Self-Administration by a Rhesus Monkey after Morphine Immunisation," *Nature*, 252: 708-710 (1974).
Boyer et al., "Adenovirus-Based Genetic Vaccines for Biodefense," *Human Gene Therapy*, 16: 157-168 (2005).
Boyer et al., "Comparison of the Efficacy of a Six Genetic Anti-Plaque Vaccine Candidates Against a Lethal Respiratory Tract Challenge with *Yersinia pestis*," *Molecular Therapy*, 15(1): S289 (2007).
Byrnes-Blake et al., "Generation of Anti-(+) Methamphetamine Antibodies is not Impeded by (+) Methamphetamine Administration During Active Immunization of Rats," *International Immunopharmacology*, 1: 329-338 (2001).
Bunce, C., "Xenova: TA_NIC: Safety, Immunogenicity and Early Sign of Efficacy," 1$^{st}$ UKNSCC [Online] retrieved from the Internet: URL: http://www.uknscc.org/2005_uknscc/speakers/Campbell_bunce.html> on Aug. 10, 2009.
Calcedo et al., "Host Immune Responses to Chronic Adenovirus Infections in Human and Nonhuman Primates," *Journal of Virology*, 83(6): 2623-2631 (2009).
Carrera et al., "Investigations Using Immunization to Attenuate the Psychoactive Effects of Nicotine," *Bioorganic & Medicinal Chemistry*, 12: 563-570 (2004).
Carrera et al., "Evaluation of the Anticocaine Monoclonal Antibody GNC92H2 as an Immunotherapy for Cocaine Overdose," *Pharmacol. Biochem. Behav.*, 81: 709-714 (2005).
Carrera et al., "Cocaine Vaccines: Antibody Protection Against Relapse in a Rat Model," *Proc. Nat. Acad. Sci. USA*, 97: 6202-6206 (2000).
Carrera et al., "A Second-Generation Vaccine Protects Against the Psychoactive Effects of Cocaine," *Proc. Natl. Acad. Sci USA*, 98: 1988-1992 (2001).
Cerny et al., "Anti-Nicotine Abuse Vaccines in the Pipeline: An Update," *Expert Opinion on Investigational Drugs*, 17(5): 691-696 (2008).
Cerny, T., "Anti-Nicotine Vaccination: Where Are We?," *Recent Results Cancer Res.*, 166: 167-175 (2005).
Chavdarian et al., "Bridged Nicotines. Synthesis of cis-2,3,3a,4,5,9b-Hexahydro-1-methyl-1H-pyrrolo[2,3-f]quinoline," *J. Org. Chem.*, 48: 492-494 (1983).
Chawla et al., "Adenovirus-vectored Vaccines," *Expert Opinion on Therapeutic Patents*, 18(3): 293-307 (Mar. 2008).
Chirmule et al., "Immune Responses to Adenovirus and Adeno-Associated Virus in Humans," *Gene Therapy*, 6: 1574-1583 (1999).
Cohen, J.,"Promising AIDS Vaccine's Failure Leaves Field Reeling," *Science*, 318: 28-29 (2007).
Cornuz et al., "A Vaccine Against Nicotine for Smoking Cessation: A Randomized Controlled Trial," *PLoS. One.*, 3(6): e2547 (2008).
Crystal et al., "Administration of an Adenovirus Containing the Human *CFTR* cDNA to the Respiratory Tract of Individuals with Cystic Fibrosis," *Nature Genetics*, 8: 42-51 (1994).

(56) References Cited

OTHER PUBLICATIONS

Cui et al., "Microparticles and Nanoparticles as Delivery Systems for DNA Vaccines," *Critical Reviews in Therapeutic Drug Carrier Systems*, 20(2&3): 103-137 (2003).
Curiel et al., "High-Efficiency Gene Transfer Mediated by Adenovirus Coupled to DNA-Polylysine Complexes," *Human Gene Therapy*, 3:147-154 (1992).
Cutler et al., "Cytokine Therapy," *Ann. NY Acad. Sci.*, 1056: 16-29 (2005).
Defer et al., "Human Adenovirus-Host Cell Interactions: Comparative Study with Members of Subgroups B and C," *Journal of Virology*, 64(8): 3661-3673 (1990).
Degenhardt et al., "Toward a Global View of Alcohol, Tobacco, Cannabis, and Cocaine Use: Findings from the WHO World Mental Health Surveys," *PLoS. Medicine*, 5(7): e141 (2008).
Duryee et al., "Immune Responses to Methamphetamine by Active Immunization with Peptide-Based, Molecular Adjuvant-Containing Vaccines," *Vaccine*, 27: 2981-2988 (2009).
Elmore et al., "A Computational Study of Nicotine Conformations in the Gas Phase and in Water," *J. Org. Chem.*, 65: 742-747 (2000).
Evans et al., "Arterial and Venous Cocaine Plasma Concentrations in Humans: Relationship to Route of Administration, Cardiovascular Effects and Subjective Effects," *The Journal of Pharmacology and Experimental Therapeutics*, 279(3): 1345-1356 (1996).
Evans et al., "Pharmacokinetics of Intravenous Cocaine Across the Menstrual Cycle in Rhesus Monkeys," *Neuropsychopharmacology*, 29: 1889-1900 (2004).
Evans et al., "Pharmacokinetics of Repeated Doses of Intravenous Cocaine Across the Menstrual Cycle in Rhesus Monkey," *Pharmacology, Biochemistry and Behavior*, 83: 56-66 (2006).
Fang et al., "Stable Antibody Expression At Therapeutic Levels Using the 2A Peptide" *Nature Biotechnology*, 23(5): 584-590 (2005).
Farina et al., "Replication-Defective Vector Based on a Chimpanzee Adenovirus," *Journal of Virology*, 75(23): 11603-11613 (2001).
Fifis et al., "Short Peptide Sequences Containing MHC Class I and/or II Epitopes Linked to Nano-Beads Induce Strong Immunity and Inhibition of Growth of Antigen-Specific Tumour Challenge in Mice," *Vaccine*, 23: 258-266 (2004).
Fiore et al., "Clinical Practice Guideline: Treating Tobacco Use and Dependence," *U.S. Dept. of Health and Human Services, Public Health Service*, (2000).
Fiore, M., "Treating Tobacco Use and Dependence: An Introduction to the US Public Health Service Clinical Praactice Guideline," *Respiratory Care*, 45(10): 1196-1199 (2000).
Fox et al., "Efficacy of a Therapeutic Cocaine Vaccine in Rodent Models," *Nature Medicine*, 2(10): 1129-1132 (1996).
Garcea et al., "Virus-Like Particles as Vaccines and Vessels for the Delivery of Small Molecules," *Current Opinion in Biotechnology*, 15: 513-517 (2004).
Gard et al., "Immunization with Inactivated Measles Virus Vaccine," *Arch. Gesamte Virusforsch.*, 16: 315-323 (1965).
Gell et al., "Studies on Hypersensitivity: IV. The Relationship Between Contact and Delayed Sensitivity: A Study on the Specificity of Cellular Immune Reactions," *J. Exp. Med.*, 113: 571-585 (1961).
Glassco et al., "Synthetsis, Optical Resolution, Absolute Configuration, and Preliminary Pharmacology of (+)- and (−)-cis-2,3,3a,4,5,9b-Hexahydro-1-methyl-1H-pyrrolo-[3,2-h]isoquinoline, a Structural Analog of Nicotine," *J. Med. Chem.*, 36: 3381-3385 (1993).
Good et al., "Preparation of Hapten-Modified Protein Antigens," *Selected Methods in Cellular Immunology*: 343-350, (1980).
Greber et al., "The Role of the Nuclear Pore Complex in Adenovirus DNA Entry," *The EMBO Journal*, 16(19): 5998-6007 (1997).
Hackett et al., "Antivector and Antitransgene Host Responses in Gene Therapy," *Current Opinion in Molecular Therapy*, 2(4): 376-382 (2000).
Hackett et al., "Adenovirus Vectors for Gene Therapy," *Gene Therapy: Therapeutic Mechanisms and Strategies, Second Edition*: 17-40, (2004).
Hardin et al., Pharmacodynamics of a Monoclonal Antiphencyclidine Fab with Broad Selectivity for Phencyclidine-Like Drugs, *J. Pharmacol. Exp. Ther.*, 285: 1113-1122 (1998).
Harvey et al., "Variability of Human Systemic Humoral Immune Responses to Adenovirus Gene Transfer Vectors Administered to Different Organs," *Journal of Virology*, 73(8): 6729-6742 (1999).
Harvey et al., "Cellular Immune Responses of Healthy Individuals to Intradermal Administration of an E1-E3-Adenovirus Gene Transfer Vector," *Human Gene Therapy*, 10: 2823-2837 (1999).
Harvey et al., "Airway Epithelial CFTR mRNA Expression in Cystic Fibrosis patients after Repetitive Administration of a Recombinant Adenovirus," *The Journal of Clinical Investigation*, 104(9): 1245-1255 (1999).
Harvey et al., "Safety of Local Delivery of Low- and Intermediate-Dose Adenovirus Gene Transfer Vectors to Individuals with a Spectrum of Morbid Conditions," *Human Gene Therapy*, 13: 15-63 (2002).
Hashimoto et al., "Induction of Protective Immunity to Anthrax Lethal Toxin with a Nonhuman Primate Adenovirus-Based Vaccine in the Presence of Preexisting Anti-Human Adenovirus Immunity," *Infection and Immunity*, 73(10): 6885-6891 (2005).
Hatsukami et al., "Safety and Immunogenicity of a Nicotine Conjugate Vaccine in Current Smokers," *Clinical Pharmacology & Therapeutics*, 78(5): 456-467 (2005).
Hieda et al., "Active Immunization Alters the Plasma Nicotine Concentration in Rats," *The Journal of Pharmacology and Experimental Therapeutics*, 283(3): 1076-1081 (1997).
Hieda et al., "Immunization of Rats Reduces Nicotine Distribution to Brain," *Psychopharmacology*, 143: 150-157 (1999).
Hildinger et al., "Hybrid Vectors Based on Adeno-Associated Virus Serotypes 2 and 5 for Muscle-Directed Gene Transfer," *Journal of Virology*, 75(13): 6199-6203 (2001).
Hirschowitz et al., "Adenovirus-Mediated Expression of Melanoma Antigen gp75 as Immunotherapy for Metastic Melanoma," *Gene Therapy*, 5: 975-983 (1998).
Hodges et al., Effect of Heat and Sodium Dodecyl Sulfate on Solubilization of Proteins before Two-Dimensional Polyacrylamide Gel Electrophoresis, *Clinical Chemistry*, 30(12): 2003-2007 (1984).
Hoff et al, "Adenovirus-based Transient Expression Systems for Peritoneal Membrane Research", *Peritoneal Dialysis International*, 26(5): 547-558 (2006).
Ino et al., "Positional linker effects in haptens for cocaine immunopharmacotherapy," *Bioorganic & Medicinal Chemistry Letters*, 17: 4280-4283 (2007).
Jegerlehner et al., "Regulation of IgG Antibody Responses by Epitope Density and CD21-Mediated Costimulation," *Eur. J. Immunol.*, 32: 3305-3314 (2002).
Jiang et al., "Novel Chitosan Derivative Nanoparticles Enhance the Immunogenicity of a DNA Vaccine Encoding Hepatitis B Virus Core Antigen in Mice," *The Journal of Gene Medicine*, 9: 253-264 (2007).
Jooss et al., "Immunity to Adenovirus and Adeno-Associated Viral Vectors: Implications for Gene Therapy," *Gene Therapy*, 10: 955-963 (2003).
Kantak et al., "Evaluation of Anti-Cocaine Antibodies and a Cocaine Vaccine in a Rat Self-Administration Model," *Psychopharmacology* 148: 251-262 (2000).
Kantor et al., "Studies on Artificial Antigens: I. Antigenicity of DNP-Polylysine and DNP Copolymer of Lysine and Glutamic Acid in Guinea Pigs," *J. Exp. Med.*, 117: 55-69 (1963).
Keyler et al., "Enhanced Immunogenicity of a Bivalent Nicotine Vaccine," *International Immunopharmacology*, 8: 1589-1594 (2008).
Kikuchi et al., "Dendritic Cells Modified to Express CD40 Ligand Elicit Therapeutic Immunity Against Preexisting Murine Turmors," *Blood*, 96(1): 91-99 (2000).
Kikuchi et al., "Dendritic Cells Genetically Modified to Express CD40 Ligand and Pulsed with Antigen Can Initiate Antigen-Specific Humoral Immunity Independent of CD4[+] T Cells," *Nature Medicine*, 6(10): 1154-1159 (2000).

(56) References Cited

OTHER PUBLICATIONS

Killian et al., "Effects of Passive Immunization Against Morphine on Heroin Self-Administration," *Pharmacology, Biochemistry & Behavior*, 9: 347-352 (1978).
Kinsey et al., "Anti-Drug Vaccines to Treat Substance Abuse," *Immunology and Cell Biology*, 87: 309-314 (2009).
Kleber et al., "Treatment of Patients with Substance Abuse Use Disorders, Second Edition" *Am. J. Psych.*, 164(4 Suppl.): 5-123 (2007).
Koob et al., "Drug Abuse: Hedonic Homeostatic Dysregulation," *Science*, 278: 52-58 (1997).
Krause et al., "Epitopes Expressed in Different Adenovirus Capsid Proteins Induce Different Levels of Epitope-Specific Immunity," *Journal of Virology*, 80(11): 5523-5530 (2006).
Kurachi e al., "Characterization of capsid-modified adenovirus vectors containing heterologous peptides in the fiber knob, protein IX, or hexon," *Gene Therapy*, 14: 266-274 (2007).
Le Houezec, J., "Why a Nicotine Vaccine?" *Clinical Pharmacology & Therapeutics*, 78: 453-455 (2005).
Leopold et al., "Dynein- and Microtubule-Mediated Translocation of Adenovirus Serotype 5 Occurs after Endosomal Lysis," *Human Gene Therapy*, 11: 151-165 (2000).
Leopold et al., "Neutralized Adenovirus-Immune Complexes Can Mediate Effective Gene Transfer via an Fc Receptor-Dependent Infection Pathway," *Journal of Virology*, 80(20): 10237-10247 (2006).
Leopold, P., "Microtubule-Dependent Motility uring Intracellular Trafficking of Vector Genome to the Nucleus: Subcellular Mimicry in Virology and Nanoengineering," *Nanotechnology in Biology and Medicine*: 34:1-17, (2007).
Mack et al., "Circumvention of Anti-Adenovirus Neutralizing Immunity by Administration of an Adenoviral Vector of an Alternate Serotype," *Human Gene Therapy*, 8: 99-109 (1997).
Maizel et al., "The Polypeptides of Adenovirus," *Virology*, 36: 126-136 (1968).
Malin et al., "Passive Immunization Against Nicotine Prevents Nicotine Alleviation of Nicotine Abstinence Syndrome," *Pharmacology, Biochemistry and Behavior*, 68: 87-92 (2001).
Malin, D., "Nicotine Dependence Studies with a Laboratory Model," *Pharmacology, Biochemistry and Behavior*, 70: 551-559 (2001).
Martell et al., "Cocaine Vaccine for the Treatment of Cocaine Dependence in Methadone-Maintained Patients: A Randomized, Double-Blind, Placebo-Controlled Efficacy Trial," *Arch. Gen. Psychiatry*, 66(10): 1116-1123 (2009).
Mastrangeli et al., "'Sero-Switch' Adenovirus-Mediated In Vivo Gene Transfer: Circumvention of Anti-Adenovirus Humoral Immune Defenses Against Repeat Adenovirus Vector Administration by Changing the Adenovirus Serotype," *Human Gene Therapy*, 7: 79-87 (1996).
Maurer et al., "Vaccine Against Nicotine: An Emerging Therapy for Tobacco Dependence," *Expert Opinion on Investigational Drugs*, 16(11): 1775-1783 (2007).
McKenzie et al., "Identification and Characterization of Single Chain Anti-Cocaine Catalytic Antibodies," *J.Mol. Biol.*, 365: 722-731 (2007).
Mets et al., "A Catalytic Antibody Against Cocaine Prevents Cocaine's Reinforcing and Toxic Effects in Rats," *Proc. Natl. Acad. Sci.*, 95: 10176-10181 (1998).
Minigo et al., "Poly-$_L$-lysine-coated nanoparticles: A potent delivery system to enhance DNA vaccine efficacy," *Vaccine*, 25: 1316-1327 (2007).
Mittereder et al., "Evaluation of the Concentration and Bioactivity of Adenovirus Vectors for Gene Therapy," *Journal of Virology*, 70(11): 7498-7509 (1996).
Miyazawa et al., "Adenovirus Serotype 7 Retention in a Late Endosomal Compartment prior to Cytosol Escape Is Modulated by Fiber Protein," *Journal of Virology*, 75(3): 1387-1400 (2001).
Mottram et al., "Type 1 and 2 Immunity Following Vaccination Is Influenced by Nanoparticle Size: Formulation of a Model Vaccine for Respiratory Syncytial Virus," *Molecular Pharmaceutics*, 4(1): 73-84 (2007).
Muller, R., "Determination of Affinity and Specificity of Anti-Hapten Antibodies by Competetive Radioimmunoassay," *Methods in Enzymology*, 92: 589-601 (1983).
Mumper et al., "Genetic immunization by jet injection of targeted pDNA-coated nanoparticles," *Methods*, 31: 255-262 (2003).
Ninalga et al., "CpG Oligonucleotide Therapy Cures Subcutaneous and Orthotopic Tumors and Evokes Protective Immunity in Murine Bladder Cancer," *J. Immunother.*, 28(1): 20-27 (2005).
Norman et al., "A Chimeric Human/Murine Antococaine Monoclonal Antibody Inhibits the Distribution of Cocaine to the Brain in Mice," *The Journal of Pharmacology and Experimental Therapeutics*, 320(1): 145-153 (2007).
Ochoa et al., "Protective immunity of biodegradable nanoparticle-based vaccine against an experimental challenge with *Salmonella enteritidis* in mice," *Vaccine*, 25: 4410-4419 (2007).
Pagona et al., "Carbon Nanotubes: Materials for Medicinal Chemistry and Biotechnological Applications," *Current Medicinal Chemistry*, 13: 1789-1798 (2006).
Plikaytis et al., "Comparisons of Standard Curve-Fitting Methods to Quantitate*Neisseria meningitis* Group A Polysaccharide Antibody Levels by Enzyme-Linked Immunosorbent Assay," *Journal of Clinical Microbiology*, 29(7): 1439-1446 (1991).
Proksch et al., "Anti-Phencyclidine Monoclonal Antibodies Provide Long-Term Reductions in Brain Phencyclidine Concentrations during Chronic Phencyclidine Administration in Rats," *The Journal of Pharmacology and Experimental Therapeutics*, 292: 831-837 (2000).
Redwan et al., "Expression and Characterization of a Humanized Cocaine-Binding Antibody, " *Biotechnology and Bioengineering*, 82(5): 612-8 (2003).
Ribeiro et al., "PLGA-dendron nanoparticles enhance immunogenicity but not lethal antibody production of a DNA vaccine against anthrax in mice," *International Journal of Pharmaceutics*, 331: 228-232 (2007).
Roiko et al., "Combined Active and Passive Immunization Enhances the Efficacy of Immunotherapy Against Nicotine in Rats," *The Journal of Pharmacology and Experimental Therapeutics*, 325(3): 985-993 (2008).
Ross et al., "Pharmacotherapy of Addictive Disorders," *Clinical Nueropharmacology*, 32(5): 277-289 (2009).
Roy et al., "Creation of a panel of vectors based on ape adenovirus isolates," *The Journal of Gene Medicine*, 13: 17-25 (2011).
Russell et al., "The Preparation and Properties of Adenovirus Cores," *Journal of General Virology*, II: 35-46 (1971).
Salk et al., "Control of Influenza and Poliomyelitis with Killed Virus Vaccines," *Science*, 195: 834-847 (1977).
Sanderson et al., "Immunization to nicotine with a peptide-based vaccine composed of a conformationally biased agonist of C5a as a molecular adjuvant," *International Immunopharmacology*, 3(1): 137-146 (2003).
Sondhi et al., "Enhanced Survival of the LINCL Mouse Following CLN2 Gene Transfer Using the rh.10 Rhesus Macaque-derived Adeno-associated Virus Vector," *Molecular Therapy*, 15(3): 481-491 (2007).
Stewart, "Pathways to relapse: the neurobiology of drug- and stress-induced relapse to drug-taking," *Journal of Psychiatry and Neuroscience*, 25(2): 125-136 (2000).
Takahashi et al., "Quantitation of adenovirus type 5 empty capsids," *Analytical Biochemistry*, 349: 208-217 (2006).
Tertilt et al., "Co-Administration of an Adenovirus Encoding the B Cell Stimulating Factor BAFF with Heat-Inactivated *Pseudomonas aeruginosa* Leads to Increased Anti-pseudomonal Humoral Immunity," *Molecular Therapy*, 9(Suppl. 1): S210 (2004).
Vigne et al., "RGD Inclusion in the Hexon Monomer Provides Adenovirus Type 5-Based Vectors with a Fiber Knob-Independent Pathway for Infection", *Journal of Virology, American Society for Microbiology*, 73(6): 5156-5161 (1999).
Vincent et al., "Rapid Assessment of Adenovirus Serum Neutralizing Antibody Titer Based on Quantitative, Morphometric Evalua-

(56) References Cited

OTHER PUBLICATIONS tion of Capsid Binding and Intracellular Trafficking: Population Analysis of Adenovirus Capsid Association with Cells Is Predictive of Adenovirus Infectivity," *Journal of Virology*, 75(3): 1516-1521 (2001).

Volkow et al., "Relationship Between Subjective Effects of Cocaine and Dopamine Transporter Occupancy," *Nature*, 386: 827-830 (1997).

Votaw et al., "Measurement of Dopamine Transporter Occupancy for Multiple Injections of Cocaine Using a Single Injection of [F-18]FECNT," *Synapse*, 44: 203-210 (2002).

Waldmann, T., "The biology of interleukin-2 and interleukin-15: implications for cancer therapy and vaccine design," *Nature Reviews Immunology*, 6: 595-601 (2006).

Wee et al., "$\alpha$1-Noradrenergic System Role in Increased Motivation for Cocaine Intake in Rats with Prolonged Access," *European Neuropsychopharmacology*, 18: 303-311 (2008).

Wold et al., "Immune Responses to Adenoviruses: Viral Evasion Mechanisms and their Implications for the Clinic," *Current Opinion in Immunology*, 11: 380-386 (1999).

Worgall et al., "Selective Expansion of Alveolar Macrophages In Vivo by Adenovirus-Mediated Transfer of the Murine Granulocyte-Macrophage Colony-Stimulating Factor cDNA," *Blood*, 93(2): 655-666 (1999).

Worgall et al., "Protection against Pulmonary Infection with *Pseudomonas aeruginosa* following Immunization with *P. aeruginosa*-Pulsed Dendritic Cells," *Infection and Immunity*, 69(7): 4521-4527 (2001).

Worgall et al., "Augmentation of pulmonary host defense against *Pseudomonas* by Fc$\gamma$RIIA cDNA transfer to the respiratory epithelium," *The Journal of Clinical Investigation*, 104(4): 409-418 (1999).

Worgall et al., "Modification to the Capsid of the Adenovirus Vector That Enhances Dendritic Cell Infection and Transgene-Specific Cellular Immune Responses," *Journal of Virology*, 78(5): 2572-2580 (2004).

Xia et al., "Combinational adenovirus-mediated gene therapy and dendritic cell vaccine in combating well-established tumors," *Cell Research*, 16: 241-259 (2006).

Yamada et al., "Novel and Cell Type-specific Gene-Drug Delivery System Using Surface Engineered Hepatitis B Virus Nano-particles," *Current Drug Targets—Infectious Disorders*, 4: 163-167 (2004).

Zhou et al., "Therapeutic potential of adenovirus as a vaccine vector for chronic virus infections," *Expert Opinion on Biological Therapy*, 6(1): 63-72 (2006).

WIPO, International Search Report in International application No. PCT/US2013/031409 dated Jun. 11, 2013, 5 pages.

\* cited by examiner

Anti-AM1 Western

Anti-Ad5 Western

△ Non-sensitized/non-immunized + PBS
▨ Pre-sensitized/HexonAM1 + nicotine
▲ Non-sensitized/non-immunized + nicotine
☐ Pre-sensitized/non-immunized + nicotine

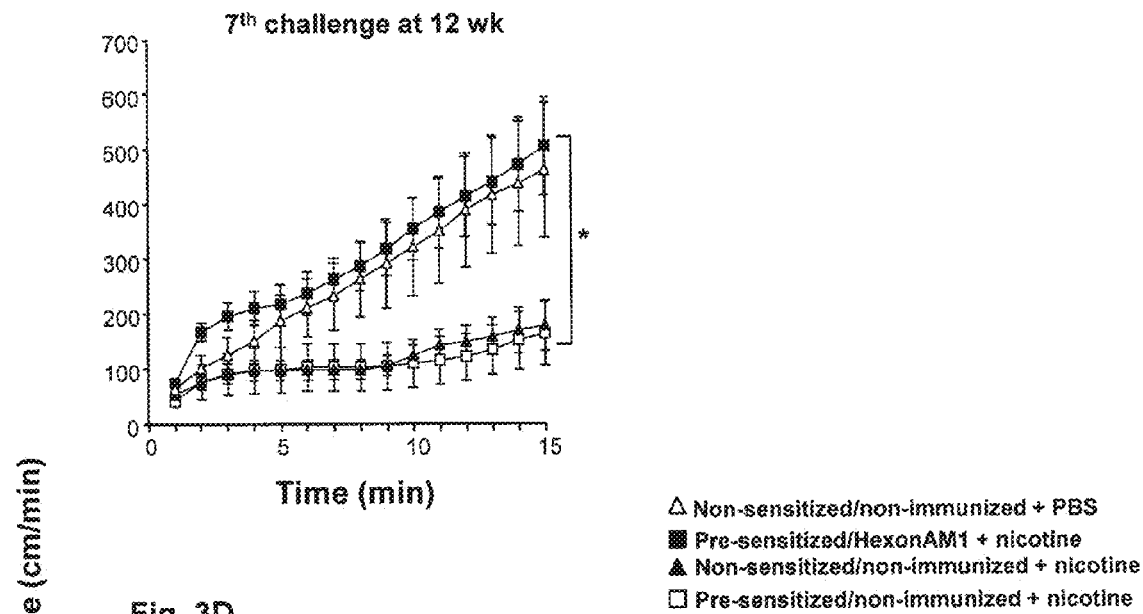
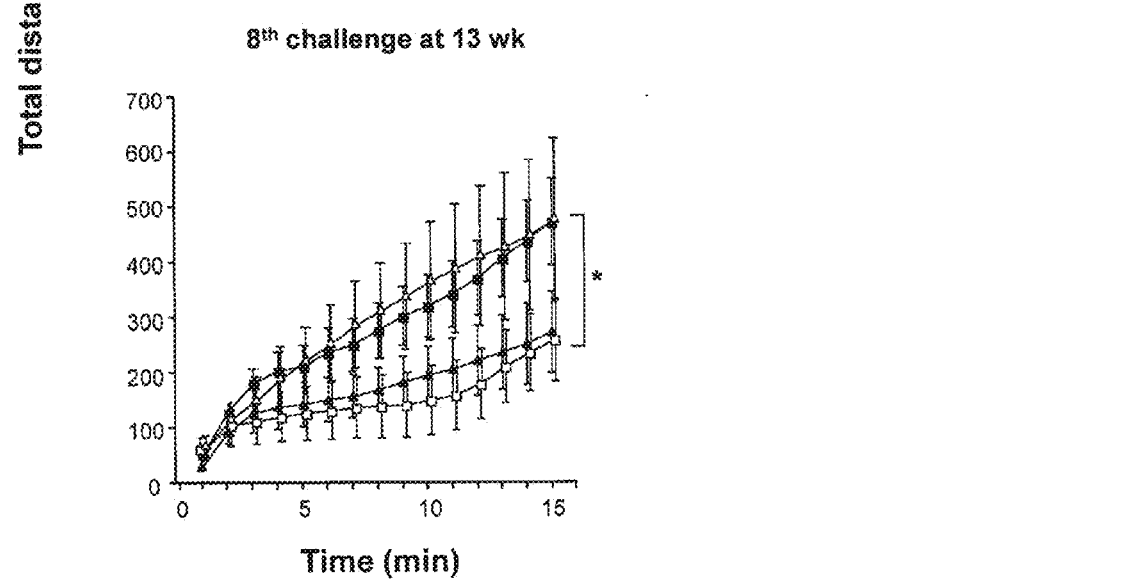

Brain

Serum

SEQUENCE LISTING

```
<160> NUMBER OF SEQ ID NOS: 1

<210> SEQ ID NO 1
<211> LENGTH: 952
<212> TYPE: PRT
<213> ORGANISM: Adenovirus type 5

<400> SEQUENCE: 1

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
                20                  25                  30

Arg Ala Thr Glu Thr Tyr Phe Ser Leu Asn Asn Lys Phe Arg Asn Pro
            35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Ala Ala Thr Ala Leu Glu Ile
    130                 135                 140

Asn Leu Glu Glu Glu Asp Asp Asp Asn Glu Asp Glu Val Asp Glu Gln
145                 150                 155                 160

Ala Glu Gln Gln Lys Thr His Val Phe Gly Gln Ala Pro Tyr Ser Gly
                165                 170                 175

Ile Asn Ile Thr Lys Glu Gly Ile Gln Ile Gly Val Glu Gly Gln Thr
            180                 185                 190

Pro Lys Tyr Ala Asp Lys Thr Phe Gln Pro Glu Pro Gln Ile Gly Glu
        195                 200                 205

Ser Gln Trp Tyr Glu Thr Glu Ile Asn His Ala Ala Gly Arg Val Leu
    210                 215                 220

Lys Lys Thr Thr Pro Met Lys Pro Cys Tyr Gly Ser Tyr Ala Lys Pro
225                 230                 235                 240

Thr Asn Glu Asn Gly Gly Gln Gly Ile Leu Val Lys Gln Gln Asn Gly
                245                 250                 255

Lys Leu Glu Ser Gln Val Glu Met Gln Phe Phe Ser Thr Thr Glu Ala
            260                 265                 270

Thr Ala Gly Asn Gly Asp Asn Leu Thr Pro Lys Val Val Leu Tyr Ser
        275                 280                 285

Glu Asp Val Asp Ile Glu Thr Pro Asp Thr His Ile Ser Tyr Met Pro
    290                 295                 300
```

```
Thr Ile Lys Glu Gly Asn Ser Arg Glu Leu Met Gly Gln Gln Ser Met
305                 310                 315                 320

Pro Asn Arg Pro Asn Tyr Ile Ala Phe Arg Asp Asn Phe Ile Gly Leu
            325                 330                 335

Met Tyr Tyr Asn Ser Thr Gly Asn Met Gly Val Leu Ala Gly Gln Ala
            340                 345                 350

Ser Gln Leu Asn Ala Val Val Asp Leu Gln Asp Arg Asn Thr Glu Leu
            355                 360                 365

Ser Tyr Gln Leu Leu Leu Asp Ser Ile Gly Asp Arg Thr Arg Tyr Phe
    370                 375                 380

Ser Met Trp Asn Gln Ala Val Asp Ser Tyr Asp Pro Asp Val Arg Ile
385                 390                 395                 400

Ile Glu Asn His Gly Thr Glu Asp Glu Leu Pro Asn Tyr Cys Phe Pro
            405                 410                 415

Leu Gly Gly Val Ile Asn Thr Glu Thr Leu Thr Lys Val Lys Pro Lys
            420                 425                 430

Thr Gly Gln Glu Asn Gly Trp Glu Lys Asp Ala Thr Glu Phe Ser Asp
            435                 440                 445

Lys Asn Glu Ile Arg Val Gly Asn Asn Phe Ala Met Glu Ile Asn Leu
450                 455                 460

Asn Ala Asn Leu Trp Arg Asn Phe Leu Tyr Ser Asn Ile Ala Leu Tyr
465                 470                 475                 480

Leu Pro Asp Lys Leu Lys Tyr Ser Pro Ser Asn Val Lys Ile Ser Asp
            485                 490                 495

Asn Pro Asn Thr Tyr Asp Tyr Met Asn Lys Arg Val Val Ala Pro Gly
            500                 505                 510

Leu Val Asp Cys Tyr Ile Asn Leu Gly Ala Arg Trp Ser Leu Asp Tyr
            515                 520                 525

Met Asp Asn Val Asn Pro Phe Asn His His Arg Asn Ala Gly Leu Arg
    530                 535                 540

Tyr Arg Ser Met Leu Leu Gly Asn Gly Arg Tyr Val Pro Phe His Ile
545                 550                 555                 560

Gln Val Pro Gln Lys Phe Phe Ala Ile Lys Asn Leu Leu Leu Leu Pro
            565                 570                 575

Gly Ser Tyr Thr Tyr Glu Trp Asn Phe Arg Lys Asp Val Asn Met Val
            580                 585                 590

Leu Gln Ser Ser Leu Gly Asn Asp Leu Arg Val Asp Gly Ala Ser Ile
            595                 600                 605

Lys Phe Asp Ser Ile Cys Leu Tyr Ala Thr Phe Phe Pro Met Ala His
    610                 615                 620

Asn Thr Ala Ser Thr Leu Glu Ala Met Leu Arg Asn Asp Thr Asn Asp
625                 630                 635                 640

Gln Ser Phe Asn Asp Tyr Leu Ser Ala Ala Asn Met Leu Tyr Pro Ile
            645                 650                 655

Pro Ala Asn Ala Thr Asn Val Pro Ile Ser Ile Pro Ser Arg Asn Trp
            660                 665                 670

Ala Ala Phe Arg Gly Trp Ala Phe Thr Arg Leu Lys Thr Lys Glu Thr
            675                 680                 685

Pro Ser Leu Gly Ser Gly Tyr Asp Pro Tyr Tyr Thr Tyr Ser Gly Ser
            690                 695                 700

Ile Pro Tyr Leu Asp Gly Thr Phe Tyr Leu Asn His Thr Phe Lys Lys
705                 710                 715                 720
```

-continued

```
Val Ala Ile Thr Phe Asp Ser Ser Val Ser Trp Pro Gly Asn Asp Arg
            725             730             735

Leu Leu Thr Pro Asn Glu Phe Glu Ile Lys Arg Ser Val Asp Gly Glu
            740             745             750

Gly Tyr Asn Val Ala Gln Cys Asn Met Thr Lys Asp Trp Phe Leu Val
        755             760             765

Gln Met Leu Ala Asn Tyr Asn Ile Gly Tyr Gln Gly Phe Tyr Ile Pro
    770             775             780

Glu Ser Tyr Lys Asp Arg Met Tyr Ser Phe Phe Arg Asn Phe Gln Pro
785             790             795             800

Met Ser Arg Gln Val Val Asp Asp Thr Lys Tyr Lys Asp Tyr Gln Gln
                805             810             815

Val Gly Ile Leu His Gln His Asn Asn Ser Gly Phe Val Gly Tyr Leu
            820             825             830

Ala Pro Thr Met Arg Glu Gly Gln Ala Tyr Pro Ala Asn Phe Pro Tyr
            835             840             845

Pro Leu Ile Gly Lys Thr Ala Val Asp Ser Ile Thr Gln Lys Lys Phe
    850             855             860

Leu Cys Asp Arg Thr Leu Trp Arg Ile Pro Phe Ser Ser Asn Phe Met
865             870             875             880

Ser Met Gly Ala Leu Thr Asp Leu Gly Gln Asn Leu Leu Tyr Ala Asn
            885             890             895

Ser Ala His Ala Leu Asp Met Thr Phe Glu Val Asp Pro Met Asp Glu
            900             905             910

Pro Thr Leu Leu Tyr Val Leu Phe Glu Val Phe Asp Val Val Arg Val
            915             920             925

His Arg Pro His Arg Gly Val Ile Glu Thr Val Tyr Leu Arg Thr Pro
    930             935             940

Phe Ser Ala Gly Asn Ala Thr Thr
945             950
```

DEVELOPMENT OF A HIGHLY EFFICIENT SECOND GENERATION NICOTINE-CONJUGATE VACCINE TO TREAT NICOTINE ADDICTION

CROSS-REFERENCE TO RELATED APPLICATIONS

This patent application claims the benefit of U.S. Provisional Patent Application No. 61/623,908 filed Apr. 13, 2012 which is incorporated by reference in its entirety herein.

STATEMENT REGARDING FEDERALLY SPONSORED RESEARCH AND DEVELOPMENT

This invention was made with Government support under Grant Numbers R01 DA025305 and RC2 DA028847 awarded by the National Institutes of Health (NIH). The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 8,523 Byte ASCII (Text) file named "718766_ST25.TXT," created on Oct. 9, 2014.

BACKGROUND OF THE INVENTION

The most widely used addictive drug in the world is tobacco, of which the principal addictive component is nicotine. Approximately 19% of adults in the U.S. smoke cigarettes, and cigarette smoking accounts for one of every five deaths in the USA (Center for Disease Control and Prevention, Morbidity and Mortality Weekly Report, *Centers for Disease Control*, 61(44): 889-894 (2012)). In the lung, cigarette smoke causes chronic obstructive pulmonary disease (COPD) and lung cancer, and smoking is associated with an increased risk of cardiovascular disease and a variety of other neoplasms (see, e.g., Alberg et al., *J. Clin. Oncol.*, 23: 3175-3185 (2005); Blanco-Cedres et al., *Am. J. Epidemiol.*, 155: 354-360 (2002); Hylkema et al., *Eur. Respir. J.*, 29: 438-445 (2007); and Sebelius K, *How Tobacco Smoke Causes Disease: the Biology and Behavioral Basis for Smoking-Attributable Disease: a Report of the Surgeon General*, U.S. Dept. of Health and Human Services (2010)). Smoking-related health care and loss of productivity cost in excess of $193 billion annually in the U.S. (Sebelius, supra).

Although each puff of cigarette smoke contains more than 4000 chemicals, the addictive properties of cigarette smoking are due to nicotine, a 162 Da alkaloid that represents 0.6-3.0% of dry weight of tobacco (see, e.g., National Cancer Institute (NCI) Tobacco Control Monograph, 9: 61 (2011); Church et al., *Environ. Health Perspect.*, 64: 111-126 (1985); and Pryor et al., *Ann. N. Y. Acad. Sci.*, 686: 12-27 (1993)). Most nicotine is pyrolized at the cigarette tip, but each cigarette typically delivers 1.0 to 1.5 mg nicotine that passes across the alveoli into the blood stream, taking about 10 to 19 seconds to reach the brain (see, e.g., Rose et al., *Drug Alcohol Depend.*, 56: 99-107 (1999); Le Houezec, J., *Int. J. Tuberc. Lung Dis.*, 7: 811-819 (2003); and Benowitz et al., *Clin. Pharmacol. Ther.*, 35: 499-504 (1984)). In the brain, nicotine binds to the nicotinic acetylcholine receptor, triggering L-tyrosine to be converted to dopamine, with resulting pleasure, reduced stress, alterations in blood pressure and heart rate, heightened alertness and increased ability to process information (see, e.g., Tammimaki et al., *Biochem. Pharmacol.*, 82(8): 808-19 (2011); Maskos, et al., *Nature*, 436: 103-107 (2005); and Benowitz, N. L., *Annu. Rev. Pharmacol. Toxicol.*, 49: 57-71 (2009)).

Despite the devastating effects of nicotine addiction, the combined current strategies with drugs and counseling to help smokers quit are mostly ineffective, with a 70 to 80% recidivism rate within 6 months (see, e.g., Fiore, M. C., et al., *Treating Tobacco Use and Dependence:* 2008 Update, U.S. Dept. of Health and Human Services). One approach to treating nicotine addiction has been to develop an anti-nicotine vaccine. Anti-nicotine vaccines attempt to generate a host immune response to evoke humoral immunity against nicotine. The challenge of this approach is that nicotine is a small molecule not seen by the immune system, and thus nicotine (or a nicotine analog) must be coupled to a larger molecule to induce an anti-nicotine immune response (Lesage et al., *AAPS. J.*, 8: E65-E75 (2006); Moreno et al., *Pharmacol. Biochem. Behav.*, 92: 199-205 (2009); and Maurer et al., *Eur. J. Immunol.*, 35: 2031-2040 (2005)). For example, AM1, a trans-3'-(hydroxymethyl) nicotine-derived nicotine hapten with a linker containing an ether moiety and a free carboxyl group for conjugation (Moreno et al., *Mol. Pharm.*, 7: 431-441 (2010)) has been attached to carriers such as tetanus toxin to create an anti-nicotine vaccine. In a rodent self-administration model, this vaccine shifted preference for nicotine self-administration (see Moreno et al., *Mol. Pharm.*, 7: 431-441 (2010)). Three active immunotherapy vaccines have been tested in clinical trials, including TA-NIC (a nicotine analog linked to cholera toxin B, Xenova), NicVAX (a nicotine analog linked to *Pseudomonas aeruginosa* exoprotein A, Nabi Pharmaceuticals), and NicQb (a nicotine analog linked to particles of the bacteriophage Qβ, Cytos Biotechnology) (see Polosa et al., *Trends Pharmacol. Sci.*, 32: 281-289 (2011); and Hatsukami et al., *Clin. Pharmacol. Ther.*, 89: 392-399 (2011)). These vaccines are well tolerated, and the individuals with the highest levels of antibodies were more likely to abstain from smoking (see Polosa et al., supra). However, all trials showed large variation among trial participants in the amount of antibody generated, and only a relatively small percentage of the participants have abstained from smoking (see Polosa et al., supra, Hatsukami et al., supra; Maurer et al., *Expert. Opin. Investig. Drugs*, 16: 1775-1783 (2007); and Pollack, A., "Antismoking Vaccine Fails in Late Trial," *The New York Times* (Jul. 18, 2011)).

Thus, there is a need for alternative compositions and methods to prevent or treat nicotine addiction. This invention provides such compositions and methods. This and other advantages of the invention will become apparent from the detailed description provided herein.

BRIEF SUMMARY OF THE INVENTION

The invention provides a conjugate comprising an isolated adenovirus hexon protein coupled to nicotine or a nicotine analog, as well as a method for using such a conjugate to induce an immune response in a human.

BRIEF DESCRIPTION OF THE SEVERAL VIEWS OF THE DRAWING(S)

Figure 1B:
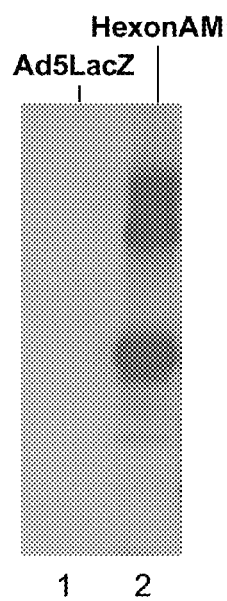
Figure 1C:
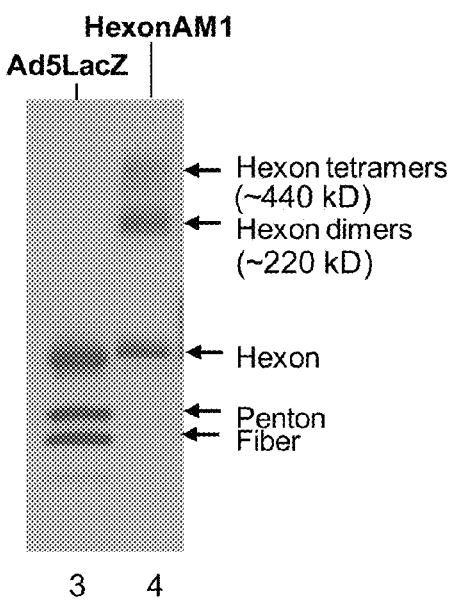

FIG. 1A is a diagram which schematically depicts a method of producing the hexon-AM1 conjugate (HexonAM1) described in Example 1. FIG. 1B is an image of a Western blot characterizing expression of HexonAM1 assessed with KLH-AM1 immunized mouse serum under reducing conditions (lane 1: Ad5LacZ; lane 2: HexonAM1). FIG. 1C is an image of a Western blot characterizing expression of HexonAM1 assessed with rabbit anti-adenovirus serotype 5 antibodies under reducing conditions (lane 3: Ad5LacZ; lane 4: HexonAM1).

Figure 2A:
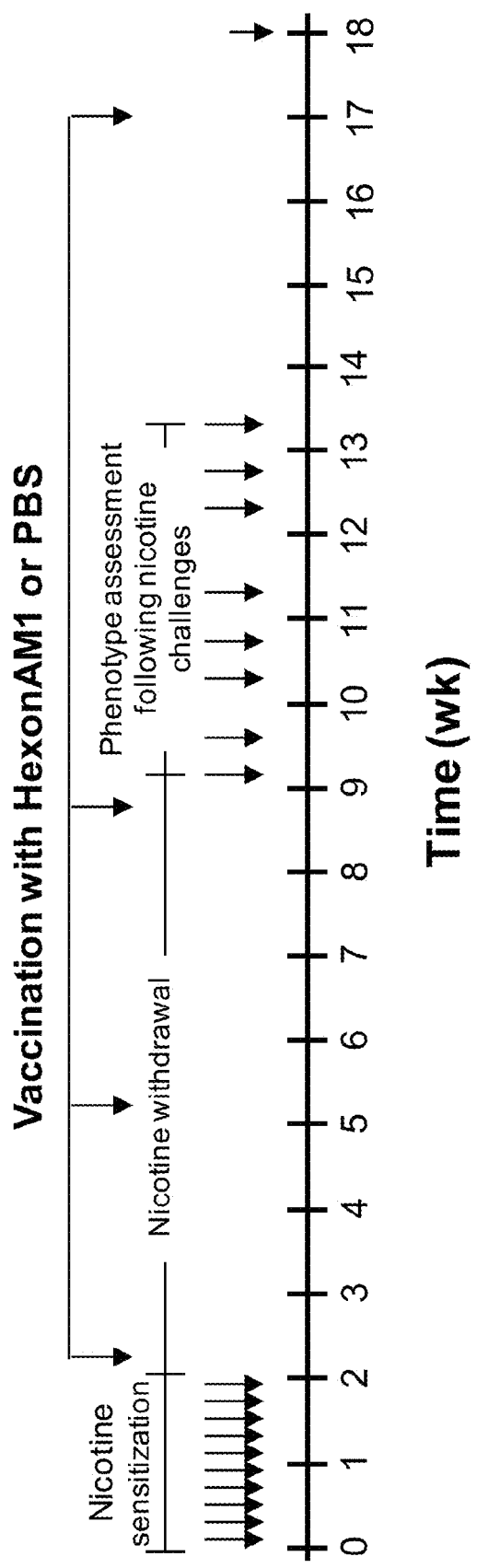
Figure 2B:
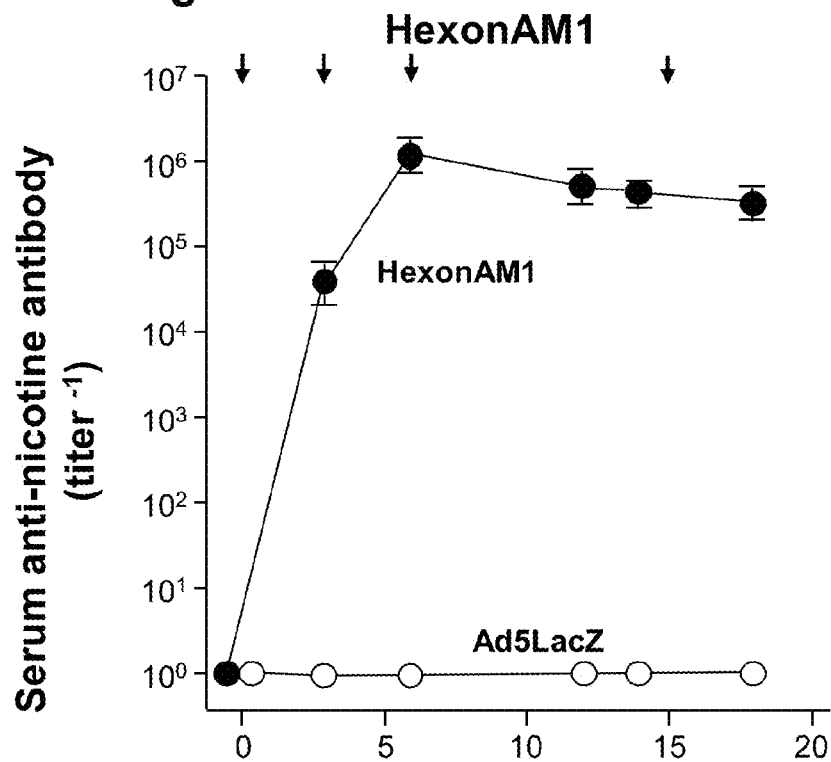
Figure 2C:
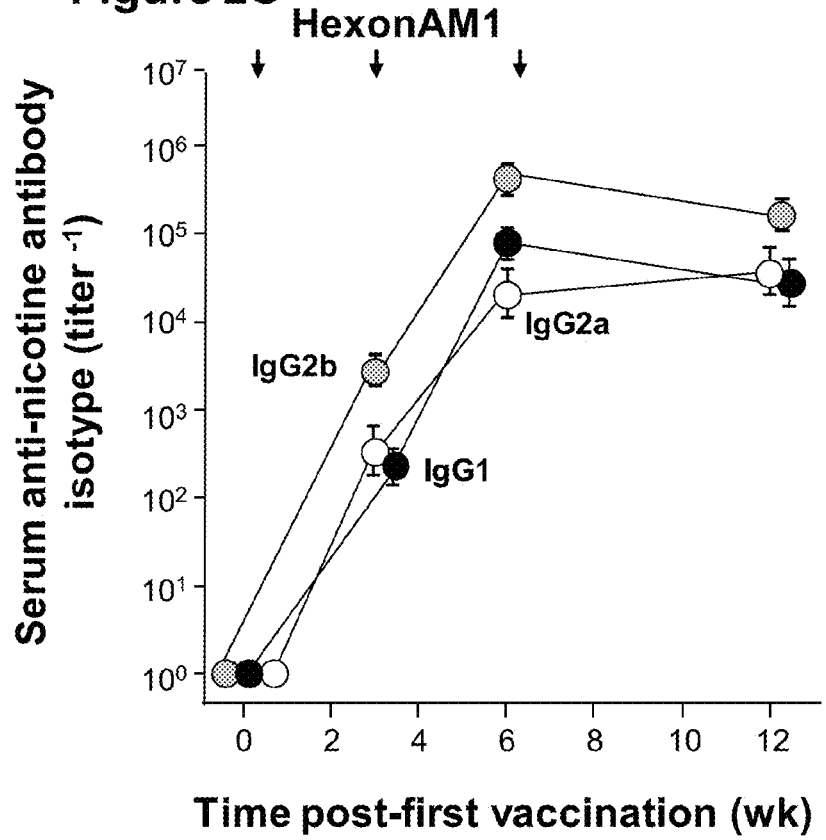

FIG. 2A is a diagram which schematically depicts an immunization method in mice using HexonAM1. The diagram includes the timing of pre-sensitization with nicotine, treatment with HexonAM1, and phenotype assessment following nicotine challenges and assessment of nicotine blood-brain distribution. FIG. 2B is a graph which depicts experimental data illustrating anti-nicotine antibody titers induced in mice after administration of HexonAM1. FIG. 2C is a graph which depicts experimental data illustrating the antibody IgG isotype titers induced in mice after administration of HexonAM1.

Figure 3A:
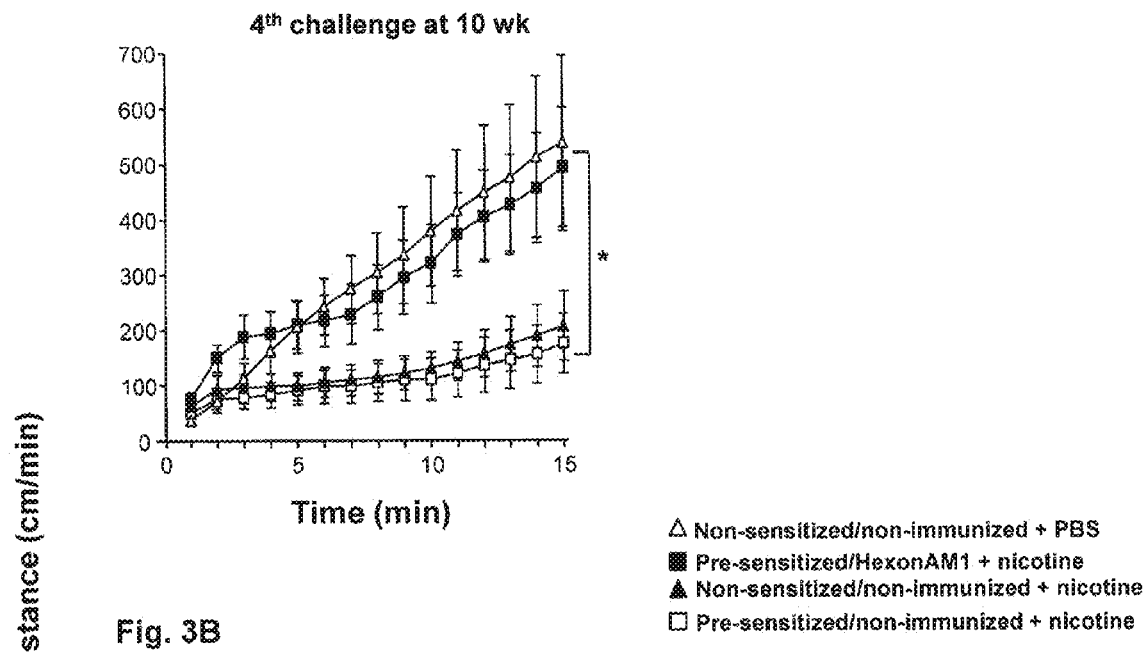
Figure 3B:
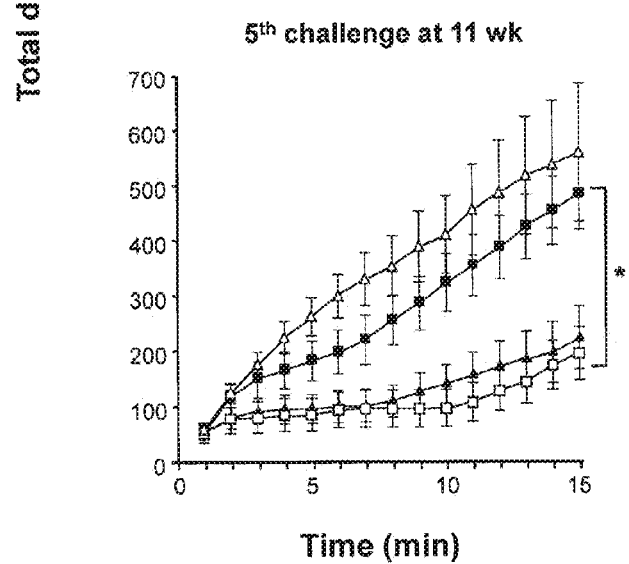

FIGS. 3A-3D are graphs which depict experimental data illustrating the cumulative distance traveled by nicotine-sensitized mice treated with HexonAM1 as compared to controls, which was assessed as a function of time post-administration of PBS or nicotine. Shown is data for pre-sensitized HexonAM1-treated mice+nicotine (■); pre-sensitized non-immunized mice+nicotine (□); non-sensitized non-immunized mice+nicotine (▲); and non-sensitized non-immunized mice+PBS (Δ). FIG. 3A depicts total distance traveled after the fourth nicotine challenge at day 74 (10 weeks post-nicotine sensitization). FIG. 3B depicts total distance traveled after the fifth nicotine challenge at day 78 (11 weeks post-nicotine sensitization). FIG. 3C depicts total distance traveled after the seventh nicotine challenge at day 88 (12 weeks post-nicotine sensitization). FIG. 3D depicts total distance traveled after the eighth nicotine challenge at day 92 (13 weeks post-nicotine sensitization).

Figure 4A:
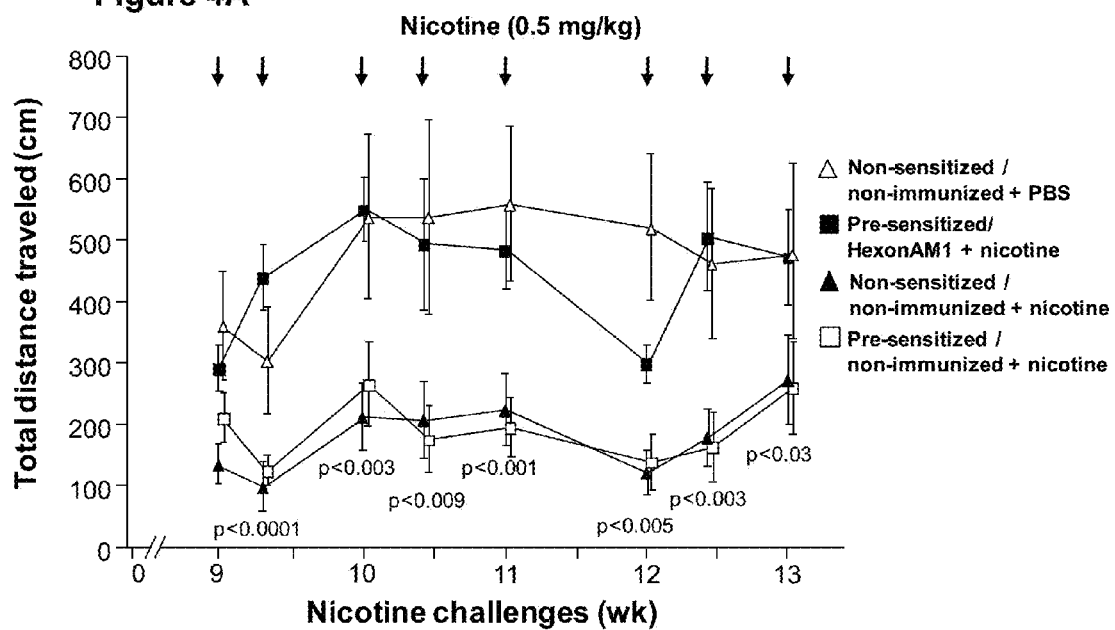
Figure 4B:
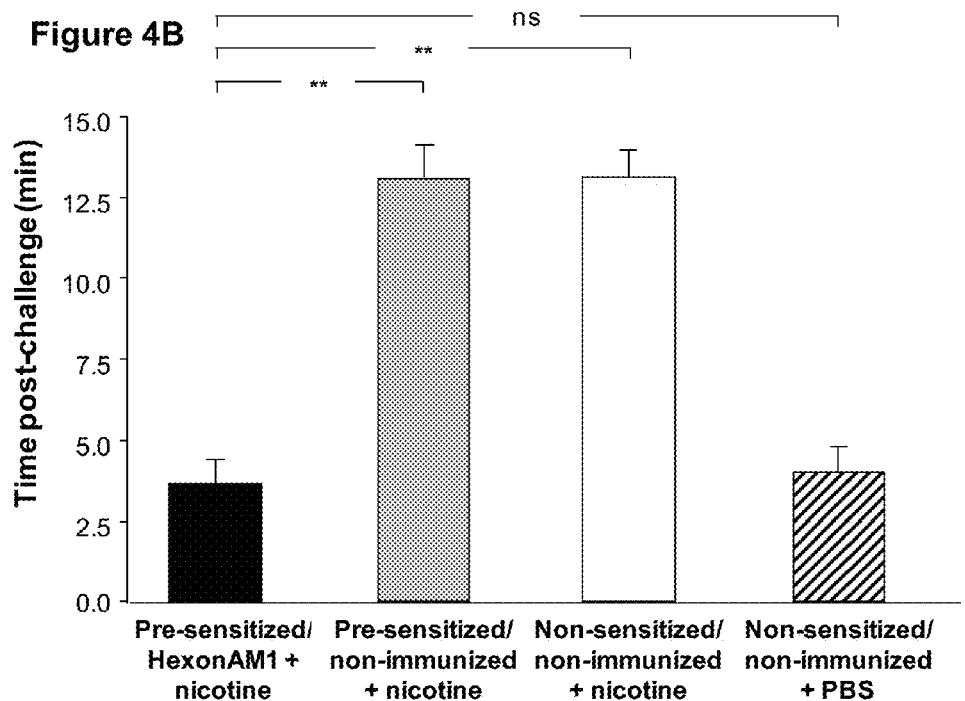

FIG. 4A is a graph which depicts experimental data illustrating locomotor activity in HexonAM1-treated mice compared to controls following repeated nicotine challenges. Shown is data for pre-sensitized HexonAM1-treated mice+nicotine (■); pre-sensitized non-immunized mice+nicotine (□); non-sensitized non-immunized mice+nicotine (▲); and non-sensitized non-immunized mice+PBS (Δ); p values are listed between the pre-sensitized mice only. FIG. 4B is a graph which summarizes the prevention of nicotine-induced hypolocomotor activity in HexonAM1-treated mice. Assessments of distance traveled by the mice post-nicotine/PBS challenge were determined in nicotine-sensitized and non-sensitized mice to compare the rapid response of the anti-nicotine antibodies in vivo. The time necessary for each nicotine-challenged mouse to travel a cumulative distance of 150 cm post nicotine challenges was averaged for each treatment group. Mean time (in minutes) required by the mice to travel 150 cm during the eight separate challenges is shown, ±SEM. Comparisons between groups were conducted by unpaired 2-tailed t-test (**=$p<0.0001$, ns=not significant).

Figure 5A:
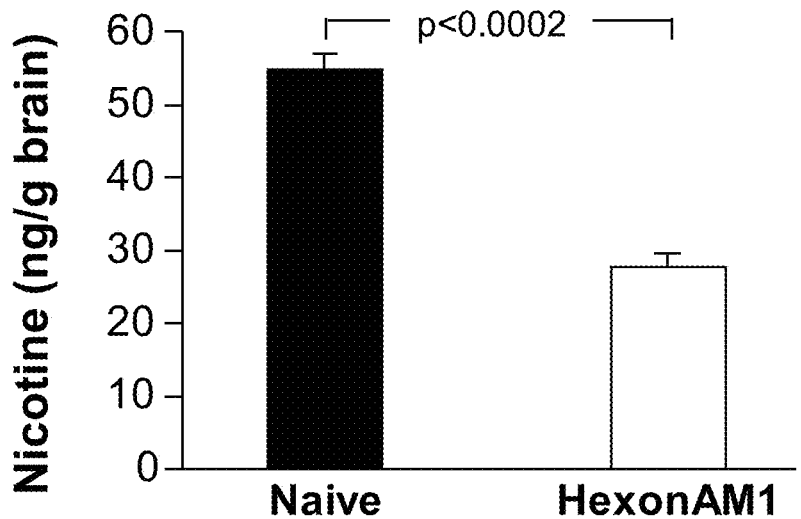
Figure 5B:
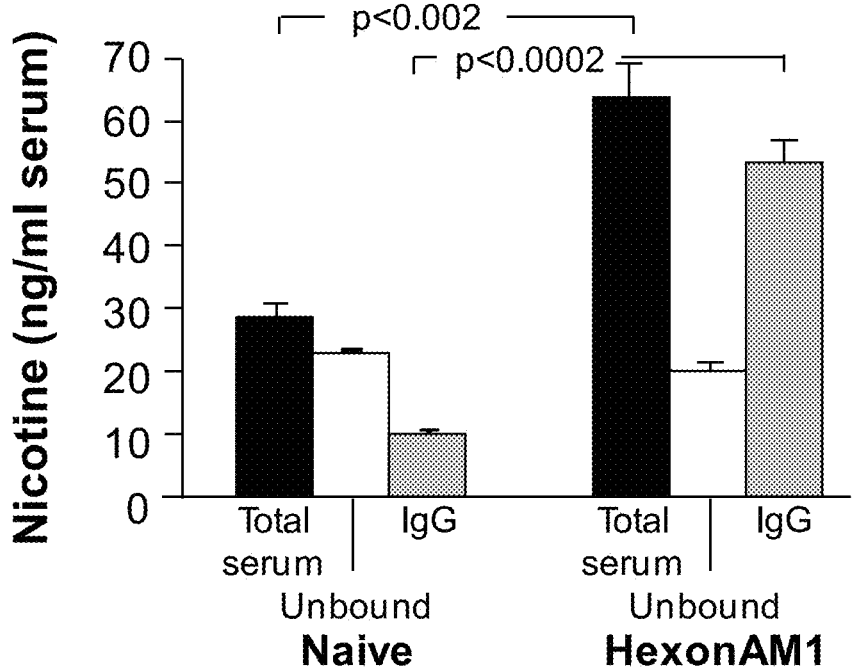

FIGS. 5A and 5B are graphs which depict experimental data illustrating the levels of nicotine in brain (FIG. 5A) and serum (FIG. 5B) of HexonAM1-treated C57B1/6 mice challenged with nicotine. Shown are nicotine levels in the brain (ng/g brain) and serum (ng/ml serum) of naive or HexonAM1-treated mice 18 weeks post-nicotine sensitization. For each group, the data includes total serum nicotine, unbound nicotine, and IgG-bound nicotine (serum, $p<0.002$; IgG, $p<0.0002$). Comparisons between groups were conducted by an unpaired 2-tailed t-test.

DETAILED DESCRIPTION OF THE INVENTION

The invention is premised, at least in part, on the appreciation that an effective anti-nicotine vaccine can be generated by conjugating nicotine, or analog thereof, to the hexon protein of an adenovirus. By coupling nicotine, or an analog thereof, to an adenovirus hexon protein, the immune system treats the antigen of the addictive drug as part of an adenovirus and generates immunity against the drug, without the need to employ an intact adenovirus or adenoviral vector.

The invention provides a conjugate which comprises, consists essentially of, or consists of an isolated adenovirus hexon protein coupled to nicotine or a nicotine analog. When the inventive conjugate consists essentially of an isolated adenovirus hexon protein coupled to nicotine or a nicotine analog, additional components can be included that do not materially affect the conjugate (e.g., protein moieties such as biotin that facilitate purification or isolation). When the conjugate consists of an isolated adenovirus hexon protein coupled to nicotine or a nicotine analog, the conjugate does not comprise any additional components (i.e., components that are not endogenous to the adenovirus hexon protein or to nicotine or the nicotine analog). By "isolated" is meant the removal of a nucleic acid or protein from its natural environment. The isolated hexon protein can comprise an intact adenovirus or any portion thereof, so long as the hexon protein is included in the isolate. For example, the isolated hexon protein can be removed from all other adenovirus proteins, with the exception of one or more other coat proteins (e.g., fiber protein and/or penton protein). Preferably the isolated hexon protein is removed from all adenovirus proteins. By "purified" is meant that a given nucleic acid or protein, whether one that has been removed from nature (including genomic DNA and mRNA) or synthesized (including cDNA) and/or amplified under laboratory conditions, has been increased in purity, wherein "purity" is a relative term, not "absolute purity." It is to be understood, however, that nucleic acids and proteins may be formulated with diluents or adjuvants and still for practical purposes be isolated. For example, nucleic acids and proteins can be mixed with an acceptable carrier or diluent when used for introduction into cells or a human.

The term "conjugate," as used herein, refers to a compound comprising two or more molecules (e.g., proteins, carbohydrates, or nucleic acid molecules) that are chemically linked. The two or molecules desirably are chemically linked using any suitable chemical bond (e.g., covalent bond). Suitable chemical bonds are well known in the art and include disulfide bonds, acid labile bonds, photolabile bonds, peptidase labile bonds, thioether, and esterase labile bonds.

While not wishing to be bound to any particular theory, it is believed that nicotine, or a nicotine analog, becomes highly immunogenic because of the inherent properties of the adenovirus hexon protein, including its size and binding affinities (both endogenous as well as with genetically engineered enhanced binding affinities). It has long been known in the art that adenoviral hexon proteins are highly immunogenic (see, e.g., Haase et al., *J. Immunol.*, 108: 483-485 (1972); and Kasel et al., *J. Immunol.*, 107: 916-919 (1971)). Modified hexon proteins have been used in the art to increase the immunogenicity of adenoviral vectors for vaccination against bacteria, protozoa, and other viruses (see, e.g., Matthews et al., *Virol. J.*, 5: 98 (2008); Matthews et al., *PLoS One*, 5: e11815 (2010); McConnell et al., *J.*

Virol., 80: 5361-5370 (2006); Palma et al., Vaccine, 29: 1683-1689 (2011); and Worgall et al., J. Clin. Invest., 115: 1281-1289 (2005)). As such, it has been hypothesized that hexon proteins may be responsible for the "adjuvant effect" observed with adenovirus vaccine preparations (see, e.g., Molinier-Frenkel et al., J. Virol., 76: 127-135 (2002)). Through conjugation to free lysines in the hexon protein, molecules such as polymers, lipids, biotin, fluorophores, and metal nanoparticles have been covalently linked to hexons (Kramp et al., Infect. Immun., 25: 771-773(1979); and Singh and Kostarelos, Trends Biotechnol., 27: 220-229 (2009)). In addition, clinical trials have explored using adenovirus capsid proteins to deliver macromolecules, such as MRI contrast agents, radiation sensitizers, and antigenic peptides (HIV-Tat) for vaccine development (see, e.g., Liepold et al., Magn. Reson. Med., 58: 871-879 (2007); Singh and Kostarelos, supra; Vasalatiy et al., Bioconjug. Chem., 19: 598-606 (2008); and Yoshioka et al., Life Sci., 83: 747-755 (2008)).

Adenovirus (Ad) is a 36 kb double-stranded DNA virus that efficiently transfers DNA in vivo to a variety of different target cell types. In the context of the inventive method, the isolated adenovirus hexon protein can be obtained or derived from an adenovirus from various origins, subtypes, or mixture of subtypes. While the adenovirus hexon protein can be obtained or derived from a non-human adenovirus (e.g., simian, avian, canine, ovine, or bovine adenoviruses), a human adenovirus preferably is used as the source of the adenovirus hexon protein. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Adenoviral serotypes 1 through 51 (i.e., Ad1 through Ad51) are available from the American Type Culture Collection (ATCC, Manassas, Va.). Preferably, in the context of the invention, the adenovirus hexon protein is obtained or derived from an adenovirus of human subgroup C, especially serotype 2 or even more desirably serotype 5. However, hexon proteins obtained or derived from non-group C adenoviruses can be used in the context of the invention. Preferred non-group C adenoviruses that can be used as the source of a hexon protein for the inventive conjugate include, for example, Ad12 (group A), Ad7 and Ad35 (group B), Ad28 and Ad30 (group D), Ad4 (group E), and Ad41 (group F). Nucleic acid sequences and amino acid sequences of hexon proteins from a variety of adenoviruses are publicly available from the National Center of Biotechnology Information (NCBI) and are disclosed in, for example, Crawford-Miksza et al., J. Virol., 70(3): 1836-1844 (1996). In one embodiment, the isolated hexon protein is obtained or derived from Ad5 and comprises the amino acid sequence of SEQ ID NO: 1.

In one embodiment, the hexon protein is obtained or derived from a disrupted adenovirus. A "disrupted" adenovirus is one that has been treated with heat and/or one or more detergents so as to render the adenovirus or adenoviral vector non-infectious in mammals. Treating adenoviruses with a mild detergent has been shown to disrupt the viral capsid and to release the nucleoprotein core, groups of nine hexon capsomers, free peripentonal hexons, penton base, and fiber capsomers (see, e.g., Molinier-Frenkel et al., J. Virol., 76: 127-135 (2002), Boulanger et al., J. Gen. Virol., 44: 783-800 (1979), Boulanger, et al., FEBS Lett., 85: 52-56 (1978), and Nermut, The Architecture of Adenoviruses, pp. 5-34, in H. S. Ginsberg (ed.), "The Adenoviruses," Plenum Press, New York, N.Y. (1984)). The adenovirus can be treated with any suitable detergent known in the art that disrupts the structure of a virus. Examples of such detergents include sodium deoxycholate (DOC), sodium dodecyl sulfate (SDS). An adenovirus can be treated with "heat" by exposing the adenovirus to a temperature above about 50° C., e.g., about 50° C. to about 70° C. The adenovirus can be exposed to a temperature of about 50° C. or higher, about 55° C. or higher, about 60° C. or higher, or about 65° C. or higher. Alternatively, or in addition, the adenovirus can be exposed to a temperature of about 70° C. or lower, about 65° C. or lower, about 60° C. or lower, or about 55° C. or lower. Thus, the adenovirus can be exposed to a temperature between any two of the above endpoints. For example, the adenovirus can be exposed to a temperature of about 50° C. to about 55° C., about 55° C. to 60° C., about 60° C. to about 65° C., about 65° C. to about 70° C.

The adenovirus hexon protein of the inventive conjugate can be a wild-type hexon protein that is purified from an intact adenovirus. The hexon protein can be purified from an intact adenovirus using protein purification methods know in the art (see, e.g., Ausubel et al. (eds.), Short Protocols in Molecular Biology, 5$^{th}$ Ed., John Wiley & Sons, New York (2002)), Such methods include, for example, chromatographic methods (e.g., ion exchange chromatography, ion exchange chromatography, HPLC, etc.), immunoprecipitation, and ultracentrifugation. Alternatively, the adenovirus hexon protein can be synthetically produced using routine recombinant DNA techniques, such as those described in, for example, Ausubel et al., supra, and Sambrook et al., Molecular Cloning, a Laboratory Manual, 3rd edition, Cold Spring Harbor Press, Cold Spring Harbor, N.Y. (2001).

In one embodiment of the invention, the adenovirus hexon protein can be modified in any number of ways to facilitate purification of the adenovirus hexon protein and/or the inventive conjugate, or to improve the biological activity of the inventive conjugate. In this respect, the adenovirus hexon protein can be labeled and/or tagged in order to facilitate purification of the adenovirus hexon protein and/or the inventive conjugate comprising the adenovirus hexon protein. Any suitable protein tag or label can be used in the invention, including, e.g., affinity tags (e.g., a poly (His) tag), solubilization tags (e.g., thioredoxin), chromatography tags (e.g., a FLAG tag), epitope tags (e.g., a c-myc tag), or fluorescence tags. A variety of protein purification tags are known in the art and can be used in the context of the invention (see, e.g., Lichty et al., Protein Expr. Purif., 41(1): 98-105 (2005)).

In another embodiment, the adenovirus hexon protein can be modified in order to facilitate polymerization or aggregation of the inventive conjugate into larger complexes via the hexon protein portion of the conjugate, which may enhance the immunogenicity of the inventive conjugate in vivo. Methods for modifying proteins to facilitate polymerization or aggregation include, but are not limited to, three-dimensional domain swapping (as described in, e.g., Ogihara et al., Proc. Natl. Acad. Sci. USA, 98(4): 1404-1409 (2001)), oxidation of cysteine residues added to an external protein loop, using bivalent crosslinkers arranged in a "head to toe" manner at the N-terminal and C-terminal of the protein, and treatment of the protein with gluteraldehyde (see, e.g., Migneault et al., BioTechniques, 37: 790-802 (2004)).

In another embodiment, the adenovirus hexon protein can be modified in order to enhance the adjuvant effects of the hexon. For example, the adenovirus hexon protein can be engineered to contain a peptide adjuvant which enhances the immune response (e.g., cellular or humoral) induced by the inventive conjugate. A variety of peptide adjuvants that can be recombinantly attached to a protein of interest (e.g., as a fusion protein) are known in the art and include, for example, heat shock protein peptides, peptides of toll-like receptor ligands (TLRs), fibronectin-binding peptide (FBP), and peptides derived from high mobility group box (HMGB1) protein 1. Peptide adjuvants also are described in, e.g., U.S. Patent Application Publication 2011/0305720. One of ordinary skill in the art will appreciate that any combination of the above-described protein modifications can be used in the context of preparing the inventive conjugate.

The inventive conjugate can comprise a full-length adenovirus hexon protein or a portion thereof. The portion of an adenovirus hexon protein can be of any size, so long as the inventive conjugate can elicit an immune response against nicotine in a human. A "portion" of an amino acid sequence comprises at least three amino acids (e.g., about 3 to about 1,000 amino acids). Preferably, a "portion" of an amino acid sequence comprises 3 or more (e.g., 5 or more, 10 or more, 15 or more, 20 or more, 25 or more, 30 or more, 40 or more, or 50 or more) amino acids, but 1,000 or less (e.g., 800 or less, 700 or less, 600 or less, 500 or less, 400 or less, 300 or less, 200 or less, or 100 or less) amino acids. Preferably, a portion of an amino acid sequence is about 3 to about 500 amino acids (e.g., about 10, 100, 200, 300, 400, or 500 amino acids), about 3 to about 300 amino acids (e.g., about 20, 50, 75, 95, 150, 175, or 200 amino acids), or about 3 to about 100 amino acids (e.g., about 15, 25, 35, 40, 45, 60, 65, 70, 80, 85, 90, 95, or 99 amino acids), or a range defined by any two of the foregoing values. More preferably, a "portion" of an amino acid sequence comprises no more than about 500 amino acids (e.g., about 3 to about 400 amino acids, about 10 to about 250 amino acids, or about 50 to about 100 amino acids, or a range defined by any two of the foregoing values).

The adenovirus hexon protein is coupled to nicotine or a nicotine analog. The nicotine analog can be a small molecule. The term "small molecule" refers to a substance or compound having a molecular weight of less than about 1,000 g/mol. Desirably, the small molecule of the invention is a hapten. A "hapten" is a small molecule capable of eliciting an immune response only when conjugated to a carrier substance, such as a protein, which can be processed by antigen presenting cells and presented to the immune system. Typically, a hapten is a modified version of a small molecule which can be coupled to the carrier substance (e.g., an adenovirus capsid protein) and presented to the immune system of a host in such a way that the immune system recognizes the unmodified small molecule.

Suitable nicotine analogs include any nicotine analog that induces an immune response in a mammal (humoral or cell-mediated). Nicotine analogs are known in the art (see, e.g., Cerny et al., *Onkologie*, 25: 406-411 (2002); Lindblom et al., *Respiration*, 69: 254-260 (2002); de Villiers et al., *Respiration*, 69: 247-253 (2002); Tuncok et al., *Exp. Clin. Psychopharmacol.*, 9: 228-234 (2001); Hieda et al., *Int. J. Immunopharmacol.*, 22: 809-819 (2000); Pentel et al., *Pharmacol. Biochem. Behav.*, 65: 191-198 (2000); Isomura et al., *J. Org. Chem.*, 66: 4115-4121 (2001); and Meijler et al., *J. Am. Chem. Soc.*, 125: 7164-7165 (2003)). For example, the nicotine analog can be N-succinyl-6-amino-(+/−)-nicotine (Castro et al., *Biochem. Biophys. Res. Commun.*, 67: 583-589 (1975)), 6-(sigma-aminocapramido)-(+/−)-nicotine (Noguchi et al., *Biochem. Biophys. Res. Commun.*, 83: 83-86 (1978)), O-succinyl-3'-hydroxymethyl-nicotine (Langone et al., *Biochemistry*, 12: 5025-5030 (1973); and *Meth. Enzymol.*, 84: 628-640 (1982)), or 3'-(hydroxymethyl)-nicotine hemisuccinate (Langone et al., supra, Abad et al., *Anal. Chem.*, 65: 3227-3231 (1993)). Additional examples of nicotine analogs suitable for use in the invention are described in U.S. Pat. Nos. 6,232,082 and 6,932,971. In a preferred embodiment, the conjugate comprises an isolated adenovirus hexon protein coupled to the nicotine analog AM1 (rac 6-((trans-1-methyl-2-(pyridin-3-yl)pyrrolidin-3-yl)methoxy)hexanoic acid) (Moreno et al., 2010, supra). Other nicotine analogs also can be used in the context of the invention, such as those described in, e.g., International Patent Application Publication WO 2009/149252.

Methods of coupling a hapten to a protein carrier are well known in the art and can be readily adapted to the coupling/conjugation of nicotine, or an analog thereof, to an adenovirus hexon protein. Such methods are described in, e.g., Sambrook et al., supra; Ausubel, et al., supra; and Harlow and Lane, *Antibodies: A Laboratory Manual*, Cold Spring Harbor Laboratory, Cold Spring Harbor, N.Y. (1988). For example, nicotine can be coupled to an adenovirus hexon protein via a linker at the 6-position or at the 1-position as previously described for nicotine-BSA conjugates and nicotine-KLH conjugates (see, e.g., Matsushita et al., *Biochem. Biophys. Res. Comm.*, 57: 1006-1010 (1974); Castro et al., *Eur. J. Biochem.*, 104: 331-340 (1980); Noguchi et al., *Biochem. Biophys. Res. Comm.*, 83: 83-86 (1978); and Isomura et al., *J. Org. Chem.*, 66: 4115-4121 (2001)). Nicotine also can be coupled to an adenovirus hexon protein via a pyridine ring as described in International Patent Application Publication WO 1999/061054, or a pyrrolidine ring as described in U.S. Pat. No. 6,232,082.

There are a large number of functional groups which can be used to facilitate the coupling/conjugation of nicotine or a nicotine analog to an adenovirus hexon protein. These include functional moieties such as carboxylic acids, anhydrides, mixed anhydrides, acyl halides, acyl azides, alkyl halides, N-maleimides, imino esters, isocyanates, amines, thiols, isothiocyanates, and others known in the art. These moieties are capable of forming a covalent bond with a reactive group of an adenovirus hexon protein. Depending upon the functional moiety used, the reactive group may be the free amino group of a lysine residue or a free thiol group of a cysteine residue on an adenovirus hexon protein which, when reacted, results in amide, amine, thioether, amidine urea, or thiourea bond formation. One of ordinary skill in the art will recognize that other suitable activating groups and conjugation techniques can be used, such as those described in Wong, *Chemistry of Protein Conjugation and Cross-Linking* (CRC Press, Inc., 1991); Hermanson, *Bioconjugate Techniques* (Academic Press, 1996); and Dick and Beurret, "Conjugate Vaccines," *Contrib. Microbiol. Immunol.*, 10: 48-114 (Karger, Basal, 1989).

Nicotine, or an analog thereof, can be coupled to an adenovirus hexon protein using a homo-bifunctional cross-linker, such as glutaraldehyde, DSG, BM[PEO]4, or BS3, which has functional groups reactive towards amine groups or carboxyl groups of an adenovirus hexon protein. Desirably, nicotine or an analog thereof is coupled to an adenovirus hexon protein by way of chemical cross-linking using a hetero-bifunctional cross-linker. Several hetero-bifunctional cross-linkers are known in the art. For example, the hetero-bifunctional cross-linker can contain a functional group which reacts with the free amino group of lysine residues of an adenovirus hexon protein, and a functional group which reacts with a native or non-native cysteine residue or sulfhydryl group present on nicotine or the nicotine analog, thereby leading to the formation of a thioether linkage. Several such hetero-bifunctional cross-linkers are known in the art and include, for example, SMPH (succinimidyl 6-[(beta-maleimidopropionamido)hexanoate]), Sulfo-MBS (m-Maleimidobenzoyl-N-hydroxysulfosuccinimide ester), Sulfo-EMCS (N-epsilon-Maleimidocaproyl-oxysulfosuccinimide ester), Sulfo-GMBS (N-gamma-Maleimidobutyryl-oxysulfosuccinimide ester), Sulfo-SIAB (sulfosuccinimidyl (4-iodoacetyl)aminobenzoate), Sulfo-SMPB (sulfosuccinimidyl 4[p-maleimidophenyl]butyrate), Sulfo-SMCC (sulfosuccinimidyl 4-(N-maleimidomethyl)cyclohexane-1-carboxylate), SVSB (succinimidyl-(4-vinylsulfone)benzoate), and SIA (N-Succinimidyl iodoacetate), which are commercially available from, for example, Pierce Thermo Fisher Scientific (Rockford, Ill., USA).

A preferred linker is a succinyl functional moiety, which forms succinimidyl ester cross-links of the antigen to epsilon amino groups exposed on an adenoviral capsid surface (Leopold et al., *Hum. Gene Ther.*, 9: 367-378 (1998) and Miyazawa et al., *J. Virol.*, 73: 6056-6065 (1999)). Examples of linkers comprising a succinyl functional moiety are N-hydroxysulfosuccinimide (Sulfo-NHS) and its uncharged analog N-hydroxysuccinimide (NHS), which are used to convert carboxyl groups to amine-reactive Sulfo-NHS esters. The presence of Sulfo-NHS esters increases the efficiency of coupling reactions mediated by carbodiimide compounds, such as EDAC (1-ethyl-3-[3-dimethylaminopropyl]carbodiimide hydrochlroide), which couple carboxyl groups to primary amines and which also can be used in conjunction with Sulfo-NHS. Maleimides, which conjugate to sulfhydryl groups, can also be used to conjugate nicotine or an analog thereof to a hexon protein of an adenovirus.

Once the adenovirus hexon protein has been coupled to nicotine or a nicotine analog, the relative extent of conjugation (also referred to as "conjugation rate") can be determined qualitatively by Western blotting for the hapten and quantitatively by mass spectrometry (e.g., MALD-TOF MS) or by measuring free functional groups on the adenovirus hexon protein by colorimetric assay.

Assuming equal affinity for antigen, there may be a direct correlation between antibody titer and vaccine efficacy. Therefore, increasing the amount of nicotine or nicotine analog that is coupled to the adenovirus hexon protein may enhance the immunogenicity thereof. Exposed lysine residues on an adenovirus hexon protein provide free amine groups that are a target for coupling to carboxylate group-containing antigens, and many of the aforementioned cross-linking reagents react preferentially with lysine residues.

It may be advantageous to add or to remove one or more lysine residues to the adenovirus hexon protein in order to maximize the attachment of hapten molecules to the adenovirus hexon protein. Thus, the adenovirus hexon protein desirably comprises one or more non-native lysine residues (e.g., 1 or more, 3 or more, 5 or more, or 7 or more lysine residues). Alternatively, or in addition, the number of non-native lysine residues can be 25 or less, e.g., 20 or less, 15 or less, or 10 or less. Thus, the number of non-native lysine residues can be bounded by any two of the above endpoints. For example, the number of non-native lysine residues can be 1-25, 3-20, 5-10, 5-15, or 7-10. When non-native lysine residues are added to a hexon protein, it is preferred that the lysine residues are incorporated into one or more flexible loops of the hexon protein. Standard molecular biology techniques which are well known in the art can be utilized to generate modified hexon proteins in accordance with the invention (see, e.g., Sambrook et al., supra; and Ausubel, et al., supra). One of ordinary skill in the art will appreciate that modifying the number of lysine residues in the hexon protein can be combined with any of the aforementioned protein modifications (e.g., to facilitate purification, to increase immunogenicity, and/or to facilitate aggregation) when preparing the inventive conjugate.

The invention provides a composition comprising, consisting essentially of, or consisting of the above-described conjugate comprising an isolated adenovirus hexon protein coupled to nicotine or a nicotine analog and a pharmaceutically acceptable (e.g. physiologically acceptable) carrier. When the composition consists essentially of the inventive conjugate and a pharmaceutically acceptable carrier, additional components can be included that do not materially affect the composition (e.g., adjuvants, buffers, stabilizers, anti-inflammatory agents, solubilizers, preservatives, etc.). When the composition consists of the inventive conjugate and the pharmaceutically acceptable carrier, the composition does not comprise any additional components. Any suitable carrier can be used within the context of the invention, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The composition can be generated in accordance with conventional techniques described in, e.g., *Remington: The Science and Practice of Pharmacy, 21st Edition*, Lippincott Williams & Wilkins, Philadelphia, Pa. (2001).

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the carrier is a buffered saline solution. More preferably, the inventive conjugate is administered in a composition formulated to protect the conjugate from damage prior to administration. For example, the composition can be formulated to reduce loss of the conjugate on devices used to prepare, store, or administer the conjugate, such as glassware, syringes, or needles. The composition can be formulated to decrease the light sensitivity and/or temperature sensitivity of the conjugate. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the conjugate, facilitate administration, and increase the efficiency of the inventive method.

The composition also can be formulated to enhance transduction efficiency. In addition, one of ordinary skill in the art will appreciate that the inventive conjugate can be present in a composition with other therapeutic or biologically-active agents. For example, factors that control inflammation, such as ibuprofen or steroids, can be part of the composition to reduce swelling and inflammation associated with in vivo administration of the conjugate. Immune system stimulators or adjuvants, e.g., interleukins, lipopolysaccharide, and double-stranded RNA, can be administered to enhance or modify the anti-nicotine immune response. Antibiotics, i.e., microbicides and fungicides, can be present to treat existing infection and/or reduce the risk of future infection, such as infection associated with drug administration.

The invention provides a method of inducing an immune response against nicotine in a human, which comprises administering an effective amount of the composition comprising the inventive conjugate to the human, whereby the nicotine or nicotine analog is presented to the immune system of the human to induce an immune response against nicotine in the human. In embodiments of the invention, the human currently smokes (i.e., is a smoker), has previously smoked but is no longer smoking, or has never smoked. The conjugate is administered to a human, whereupon an immune response against nicotine is induced. The immune response can be a humoral immune response, a cell-mediated immune response, or, desirably, a combination of humoral and cell-mediated immunity. Ideally, the immune response provides a clinical benefit upon exposure to the antigen. A "clinical benefit" can be, for example, a reduction in the physiological effects of nicotine, a reduction in the reward or pleasure associated with use of nicotine, a reduction in the likelihood of regaining an addiction to nicotine, or a prophylactic effect (i.e., smoking prevention). However, a clinical benefit is not required in the context of the invention. The inventive method further can be used for antibody production and harvesting. For example, the inventive method can be used to produce antibodies for diagnostic purposes (e.g., to detect the presence of nicotine or a nicotine analog in blood).

Any route of administration can be used to deliver the composition to the mammal. Indeed, although more than one route can be used to administer the composition, a particular route can provide a more immediate and more effective reaction than another route. Preferably, the composition is administered via injection, especially intramuscular injection. A dose of composition also can be applied or instilled into body cavities, absorbed through the skin (e.g., via a transdermal patch), inhaled, ingested, topically applied to tissue, or administered parenterally via, for instance, intravenous, peritoneal, or intraarterial administration.

The composition can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the conjugate. The composition also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

The dose of the conjugate in the composition administered to the mammal will depend on a number of factors, including the size (mass) of the mammal, the extent of any side-effects, the particular route of administration, and the like. Preferably, the inventive method comprises administering a "therapeutically effective amount" of the composition comprising the inventive conjugate described herein. A "therapeutically effective amount" refers to an amount effective, at dosages and for periods of time necessary, to achieve a desired therapeutic result. The therapeutically effective amount may vary according to factors such as the degree of nicotine addiction, age, sex, and weight of the individual, and the ability of the conjugate to elicit a desired response in the individual. In another embodiment, the inventive method can comprise administering a "prophylactically effective amount" of the composition comprising the inventive conjugate. A "prophylactically effective amount" refers to an amount effective, at dosages and for periods of time necessary, to achieve a desired prophylactic result (e.g., prevention of nicotine addiction).

A typical dose of conjugate in the composition required to achieve a particular therapeutic or prophylactic effect (i.e., prevention or treatment of nicotine addiction) can be, for example, in the range of 0.001 to 1000 µg; however, doses below or above this exemplary range are within the scope of the invention. The daily parenteral dose can be about 0.1 µg/kg to about 100 mg/kg of total body weight (e.g., about 5 µg/kg, about 10 µg/kg, about 100 µg/kg, about 500 µg/kg, about 1 mg/kg, about 50 mg/kg, or a range defined by any two of the foregoing values), preferably from about 0.3 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values), more preferably from about 1 µg/kg to 1 mg/kg of total body weight (e.g., about 3 µg/kg, about 15 µg/kg, about 75 µg/kg, about 300 µg/kg, about 900 µg/kg, or a range defined by any two of the foregoing values), and even more preferably from about 0.5 to 10 mg/kg body weight per day (e.g., about 2 mg/kg, about 4 mg/kg, about 7 mg/kg, about 9 mg/kg, or a range defined by any two of the foregoing values). Therapeutic or prophylactic efficacy can be monitored by periodic assessment of treated patients. Other dosage regimens may be useful and are within the scope of the invention. The desired dosage can be delivered by a single bolus administration of the composition, by multiple bolus administrations of the composition, or by continuous infusion administration of the composition. One of ordinary skill in the art can readily determine an appropriate conjugate dose range to treat a patient having a particular disease or disorder, such as nicotine addiction, based on these and other factors that are well known in the art.

In a preferred embodiment of the invention, the composition is administered once to the human. It is believed that a single administration of the composition will result in persistent expression of the conjugate in the mammal with minimal side effects. However, in certain cases, it may be appropriate to administer the composition multiple times during a therapeutic period and/or employ multiple administration routes, e.g., intramuscular and subcutaneous, to ensure sufficient exposure of cells to the composition. For example, the composition may be administered to the human two or more times (e.g., 2, 3, 4, 5, 6, 6, 8, 9, or 10 or more times) during a therapeutic period. When the composition is administered multiple times during a therapeutic period, each administration of the composition can be the same or different doses and can be separated by any suitable timeframe, e.g., 1 week or more, 2 weeks or more, 4 weeks or more (e.g., one month or more), 8 weeks or more, 12 weeks or more, 16 weeks or more, 24 weeks or more, 52 weeks or more, or a range defined by any two of the foregoing values.

The composition can be administered in conjunction with counseling and/or one or more additional agents that prevent or treat nicotine addiction. For example, the additional agent can be, for example, an anti-depressant, a nicotine receptor modulator, a cannabinoid receptor antagonist, an opioid receptor antagonist, a monoamine oxidase inhibitor, an anxiolytic, or any combination of these agents. Preferably, the additional agent is an anti-depressant selected from the group consisting of bupropion, doxepin, desipramine, clomipramine, imipramine, nortriptyline, amitriptyline, protriptyline, trimipramine, fluoxetine, fluvoxamine, paroxetine, sertraline, phenelzine, tranylcypromine, amoxapine, maprotiline, trazodone, venlafaxine, mirtazapine, and pharmaceutically active salts or optical isomers thereof.

The following examples further illustrate the invention but, of course, should not be construed as in any way limiting its scope.

EXAMPLE 1

This example demonstrates the preparation of a conjugate comprising an adenovirus hexon protein coupled to a nicotine analog.

A recombinant serotype adenoviral vector containing partial deletions of the E1A and E1B regions and a β-galactosidase expression cassette inserted into the E1 deletion was propagated and purified to produce Ad5LacZ (see, e.g., Rosenfeld et al., Cell, 68: 143-155 (1992)). Disruption of the adenoviral vector was carried out by treatment with lithium iodide (22% final concentration; Sigma-Aldrich, St. Louis, Mo.) in the presence of 0.17 mM sodium thiosulfate at 36° C., for 30 minutes (see, e.g., Neurath et al., J. Virol., 5, 173-178 (1970)). Disrupted capsid proteins were diluted 25-fold in 50 mM phosphate buffer pH 7.0 and mixed by vortexing. The capsid proteins were loaded onto a 5 ml pre-packed QHP anion exchange column (GE healthcare, Piscataway, N.J.) previously equilibrated with 50 mM phosphate buffer pH 7.0. The column was washed with 10 ml phosphate buffer pH 7.0. The hexon protein was eluted from the column with 15 ml 50 mM phosphate buffer pH 7.0 plus 0.4 M sodium chloride. The eluate was concentrated using an Amicon 30K concentrator (Millipore, Billerica, Mass.), diluted 25-fold with PBS, and further concentrated. Protein concentration of the purified hexon was determined by a bicinchoninic acid assay (Pierce Biotechnology, Rockford, Ill.).

The nicotine analog AM1 (rac 6-((trans-1-methyl-2-(pyridin-3-yl)pyrrolidin-3-yl)methoxy)hexanoic acid) (Moreno et al. (2010), supra) was activated overnight at 4° C. in 7.2 µl of charging solution, which was made by dissolving 2.4 mg of 1-ethyl-3-[3-dimethylaminopropyl]carbodiimide hydrochloride and 2 mg of N-hydroxysulfosuccinimide in 4 µl H$_2$O and 40 µl dimethylformamide (Hicks et al., Mol. Ther., 19, 612-619 (2011)). Conjugation of 200 µg of the purified hexon protein with charged AM1 (referred to herein as "HexonAM1") (4:1 hapten to hexon weight ratio) was carried out by incubating the hexon protein and AM1 overnight at 4° C. in 200 µl of phosphate-buffered saline, pH 7.4 (PBS). HexonAM1 was purified from unreacted small molecules by dialysis against 100 mM Tris-HCl buffer (pH 7.8) containing 20% sucrose. The amount of hexon protein eluated was quantified by a bicinchoninic acid assay (Pierce Biotechnology, Rockford, Ill.). The production of HexonAM1 is schematically depicted in FIG. 1A.

HexonAM1 was characterized by Western blot. Specifically, polyclonal antibody sera to nicotine were produced by conjugating AM1 to KLH at a ratio of 2:1 (see, e.g., Carrera et al., Nature, 378: 727-730 (1995)). The resulting AM1-KLH conjugate (0.1 mg) was formulated in complete Freund's adjuvant (CFA) (Sigma-Aldrich, St. Louis, Mo.) and intramuscularly administered to BALB/c mice. Polyclonal sera derived from a bleed of 10-week old mice were used for Western analysis of HexonAM1. Hexon-AM1 protein components were resolved by a 4 to 12% polyacrylamide SDS gel under reducing conditions, transferred to a PVDF membrane, and probed with the anti-nicotine polyclonal sera or, to assess for the adenovirus components, anti-adenovirus antibody (Abcam, Cambridge, Mass.). The membranes were developed with horseradish peroxidase-conjugated goat anti-mouse IgG (Santa Cruz Biotechnology, Santa Cruz, Calif.) and ECL reagent (GE Healthcare, Piscataway, N.J.).

Western analysis of HexonAM1 demonstrated efficient coupling of the nicotine analog to the hexon protein, as well as generation of a stable hexon-AM1 multimeric structure, as shown in FIG. 1B. The anti-adenovirus Western analysis demonstrated that HexonAM1 maintained the Ad5 hexon immunogenic structure necessary to elicit an immune response, as shown in FIG. 1C.

The results of this example demonstrate the production of the inventive conjugate and that the inventive conjugate is stable in vivo.

EXAMPLE 2

This example describes a method of inducing an immune response against nicotine in an animal model using the inventive conjugate.

To establish a mouse test model analogous to that of chronic human smokers, mice were pre-sensitized to nicotine prior to administration of HexonAM1 described in Example 1. Specifically, non-vaccinated naive C57BL/6 male mice (n=16/group) were given daily parenterally administrations of PBS or nicotine [(−) nicotine hydrogen tartrate (Sigma-Aldrich, St. Louis, Mo.), 200 µl, 0.5 mg/kg of body weight] subcutaneously in the nape of the neck 10 times over the course of 2 weeks.

Three days following the end of nicotine sensitization, C57BL/6 mice (n=8) were immunized by intramuscular injection to the quadriceps with 4 µg of HexonAM1 in 50:1 volume, formulated in 20% ADJUPLEX® adjuvant (Advanced BioAdjuvants, Omaha, Nebr.) in PBS at week 2, and boosted with the same conjugate mixture at 5, 8, and 17 weeks via intramuscular injection to the quadriceps, as shown in FIG. 2A. Blood was collected from the transected tail vein, allowed to clot, centrifuged at 10,000×g for 20 minutes, and the resulting serum was stored at −20° C.

Anti-nicotine antibody responses in treated mice were assessed using ELISA. Specifically, wells of flat bottomed 96-well EIA/RIA plates (Corning, New York, N.Y.) were coated with 100 µl of 1 mg/ml AM1-conjugated bovine serum albumin (BSA) at a ratio of 1:2 in carbonate buffer (pH 9.4) overnight at 4° C. (as described above but substituting BSA for KLH). Two-fold serial dilutions of collected mouse serum at 0, 3, 6, 12, 14, and 18 weeks were added to each well and incubated for 90 minutes at 23° C. Serum from Ad5LacZ-immunized mice was used as a negative control for all time points. The ELISA was developed as described in Hicks et al., Sci. Transl. Med., 4: 140ra87 (2012).

HexonAM1 evoked high levels of anti-nicotine antibody, as shown in FIG. 2B, producing a mean titer of $1.1 \times 10^6 \pm 7.6 \times 10^4$ and $3.1 \times 10^5 \pm 4.2 \times 10^4$ at weeks 6 and 18, respectively. Quantification of the time course of isotype-specific titers revealed anti-nicotine IgG2b, IgG1, and IgG2a titers were detectable at week 3 and increased substantially at week 6, with IgG2b titers a log higher than other isotypes, as shown in FIG. 2C.

The results of this example demonstrate that administration of the inventive conjugate can induce nicotine-specific antibody responses in vivo.

EXAMPLE 3

This example demonstrates that the inventive conjugate inhibits the locomotor effects induced by nicotine in mice.

Both pre-sensitized and non-sensitized mice from Example 2 were repeatedly challenged over a 5 week period (9 to 13 weeks post-sensitization) with nicotine (0.5 mg/kg) or PBS subcutaneously for a total of 8 nicotine challenges (n=8 mice/group). Mice were monitored for nicotine-induced changes in activity over 15 minutes using infrared beam-equipped open field chambers (20×20 cm chamber, AccuScan Instruments, Columbus, Ohio). Mice were allowed to habituate to the testing room for greater than 30 minutes prior to each test. Mice were placed in the chamber for 15 minutes to record baseline behavior. After removal from the chamber, mice were injected with PBS or nicotine (0.5 mg/kg wt) subcutaneously and returned to the chamber for 15 minutes. Locomotor activity was measured as ambulatory distance traveled in centimeters (cm).

Mice not receiving HexonAM1 and exposed to nicotine at weeks 10, 11, 12, and 13 demonstrated suppression of locomotor activity regardless of nicotine pre-sensitization, as shown in FIGS. 3A-D. In contrast, mice treated with HexonAM1 traveled a cumulative total distance over 15 minutes that was the same as the non-sensitized, non-immunized mice challenged with PBS instead of nicotine. Assessment of each of the 8 nicotine challenges in mice treated and not treated with HexonAM1 demonstrated that HexonAM1 mediated significant alleviation of nicotine-induced hypolocomotor activity at each challenge over the 5 week test period, as shown in FIG. 4A (group interaction p values: pre-sensitized HexonAM1+nicotine vs pre-sensitized non-vaccinated+nicotine, $p<0.008$, $F(1,7)=13.73$; vs non-sensitized non-vaccinated+nicotine, $p<0.002$, $F(1,7)=22.1$; vs non-sensitized non-vaccinated+PBS, $p>0.84$, $F(1,7)=0.04$; two-way ANOVA with repeated measures with Bonferroni ad-hoc comparisons). The interaction between group and day was not significant for all groups ($p>0.13$, $p>0.19$, $p>0.29$, respectively). Post-hoc analysis using the Bonferroni's multiple comparisons test showed no significance.

To summarize the above-described data into a single parameter for all eight nicotine challenges, the time required for mice to reach a total ambulatory activity of 150 cm was assessed, the results of which are shown in FIG. 4B. The time required for both pre-sensitized and non-sensitized mice that did not receive HexonAM1 to reach a total ambulatory activity of 150 cm was greater than 13 minutes on average. The time required for non-sensitized PBS-treated mice (i.e., no nicotine) to reach a total ambulatory activity of 150 cm was less than 4 minutes on average ($p<0.0001$ and $p>0.36$, respectively, compared to AM1-vaccinated mice). Naive control mice not treated with HexonAM1 exhibited a noticeable nicotine-induced suppression of ambulatory activity (206±54 cm over 15 minutes) compared to that of nicotine-challenged mice treated with HexonAM1 (494±107 cm), who showed no nicotine-induced reduction in locomotor activity similar to PBS-treated mice (538±157 cm; FIG. 3D). Interactions were significant between the HexonAM1-treated mice and non-treated mice, as shown in FIGS. 3A-3D (weeks 10, 11, 12, and 13, respectively; pre-sensitized HexonAM1+nicotine vs pre-sensitized non-vaccinated+nicotine, $p<0.0001$ for all 4 challenges, $F(14,196)=20.5$, 16.7, 10.2, 4.9 respectively, two-way ANOVA with repeated measures of time comparisons).

The results of this example demonstrate that the inventive conjugate inhibits adverse locomotor effects of nicotine.

EXAMPLE 4

This example demonstrates that administration of the inventive conjugate can shield the brains of mice from nicotine.

To assess the blood/brain distribution of nicotine in mice treated with HexonAM1 as described in Example 2, naive or HexonAM1-treated mice were anesthetized by intraperitoneal injection of ketamine (100 mg/kg) and xylazine (10 mg/kg) two minutes prior to tail vein administration of 0.4 µg of nicotine (equivalent to 1 cigarette) with 1.0 µCi [3H]nicotine (PerkinElmer, Waltham, Mass.). One minute later, the mice were sacrificed and brain and trunk blood were collected separately. Brain tissue was homogenized in PBS. 300 µl of brain homogenate and 50:1 of serum were added to separate 5 ml liquid scintillant (Ultima Gold™, PerkinElmer), assayed in triplicate for tritium, and normalized with a standard quenching curve. For the blood compartment, nicotine was normalized to serum volume, and brain was normalized to brain wet weight.

The results of this experiment are shown in FIGS. 5A and 5B. One minute after nicotine administration, 83% of the total serum nicotine (61.5±4.8 ng/ml) was IgG-bound serum nicotine (51.4±3.3 ng/ml), representing a 5.2-fold increase in IgG-bound serum nicotine as compared to naive control mice (9.6±0.4 ng/ml; $p<0.0002$). Conversely, nicotine levels in the brain of mice treated with HexonAM1 (27.8±1.3 ng/g brain) were reduced by 50% as compared to naive control mice (54.9±1.8 ng/g brain), representing a 3.9-fold reduction in the ratio of brain to blood nicotine levels in the mice treated with HexonAM1 ($p<0.002$).

The results of this example demonstrate that mice treated with the inventive conjugate sequester nicotine to the blood compartment.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A conjugate comprising an isolated adenovirus hexon protein coupled to nicotine or a nicotine analog, wherein the conjugate does not comprise an intact adenovirus.

2. The conjugate of claim 1, wherein the isolated adenovirus hexon protein is purified from an adenovirus.

3. The conjugate of claim 1, wherein the isolated adenovirus hexon protein is recombinant.

4. The conjugate of claim 1, wherein the isolated hexon protein comprises one or more additional adenovirus coat proteins.

5. The conjugate of claim 1, wherein the isolated hexon protein is removed from all adenovirus proteins.

6. The conjugate of claim 1, wherein the adenovirus is a human adenovirus.

7. The conjugate of claim 6, wherein the adenovirus is a serotype 5 adenovirus.

8. The conjugate of claim 1, wherein the isolated adenovirus hexon protein is coupled to a nicotine analog.

9. The conjugate of claim 8, wherein the nicotine analog is N-succinyl-6-amino-(+/−)-nicotine, 6-(sigma-aminocapramido)-(+/−)-nicotine, O-succinyl-3'-hydroxymethyl-nicotine, 3'-(hydroxymethyl)-nicotine hemisuccinate, or rac 6-((trans-1-methyl-2-(pyridin-3-yl)pyrrolidin-3-yl)methoxy)hexanoic acid (AM1).

10. A composition comprising the conjugate of claim 1 and a pharmaceutically acceptable carrier.

11. A method of inducing an immune response against nicotine in a human, which method comprises administering to a human an effective amount of the composition of claim 10, whereby the nicotine or nicotine analog is presented to the immune system of the human to induce an immune response against nicotine in the human.

12. The method of claim 11, wherein the composition is administered to the human once during a therapeutic period.

13. The method of claim 11, wherein the composition is administered to the human two or more times during a therapeutic period.

* * * * *